(12) United States Patent
Field

(10) Patent No.: US 7,254,555 B2
(45) Date of Patent: Aug. 7, 2007

(54) SYSTEM FOR INVOICE RECORD MANAGEMENT AND ASSET-BACKED COMMERCIAL PAPER PROGRAM MANAGEMENT

(75) Inventor: Richard G. Field, 7440 Ridgeway Rd., Golden Valley, MN (US) 55427

(73) Assignee: Richard G. Field, Golden Valley, MN (US)

( * ) Notice: Subject to any disclaimer, the term of this patent is extended or adjusted under 35 U.S.C. 154(b) by 256 days.

(21) Appl. No.: 10/145,728

(22) Filed: May 13, 2002

(65) Prior Publication Data

US 2002/0133460 A1 Sep. 19, 2002

Related U.S. Application Data

(63) Continuation of application No. 09/514,807, filed on Feb. 28, 2000, now abandoned, which is a continuation of application No. 08/336,531, filed on Nov. 9, 1994, now Pat. No. 6,073,104.

(51) Int. Cl.
*G06Q 40/00* (2006.01)

(52) U.S. Cl. ............................ 705/36 R; 705/2; 705/3; 705/4

(58) Field of Classification Search .................. 705/38, 705/37 R, 2, 3, 4
See application file for complete search history.

(56) References Cited

U.S. PATENT DOCUMENTS 4,667,292 A 5/1987 Mohlenbrock et al. ..... 364/406

(Continued)

FOREIGN PATENT DOCUMENTS

EP 0297780 1/1989

(Continued)

OTHER PUBLICATIONS

Sumant Pendharker et al, Integrating Spreadsheetswith Databases, 1993, Random House, pp. 1-15, 41-49, 69-76, and 95-115.*

(Continued)

*Primary Examiner*—Jagdish Patel
*Assistant Examiner*—Kirsten Apple

(74) *Attorney, Agent, or Firm*—Schwegman, Lundberg, Woessner & Kluth, P.A.

(57) ABSTRACT

A computerized system that will allow healthcare providers to access the commercial paper market by "selling" their patient claims to asset backed commercial paper conduits. The system generates the statistical information on the historic collection experience of the provider's claims required by both the rating agencies and the sponsors of the conduits. This statistical information has two pieces: the net collectible value matrix showing the percentage of the claim actually paid by individual payers; and a collection histogram showing the timing of the payers payments from the date of initial billing. The system also generates the accounting detail necessary for controlling and auditing the provider's participation in the commercial paper conduit program. The system tracks "periodic pools" of claims so as to be able to reconcile advances, collections, interest expense, third party fees and cash settlements between conduits and providers. This statistical information has two pieces: the net collectible value matrix showing both the percentage of the claim actually paid by individual payors and the standard deviation of this percentage; and a collection histogram showing the timing of the payors' payments from the date of initial billing.

2 Claims, 55 Drawing Sheets

U.S. PATENT DOCUMENTS

| | | | |
|---|---|---|---|
| 5,325,290 A | 6/1994 | Cauffman et al. | 364/401 |
| 5,359,509 A | 10/1994 | Little et al. | 364/401 |
| 5,361,202 A | 11/1994 | Doue | 364/413 |
| 5,383,113 A | 1/1995 | Kight et al. | 364/401 |

FOREIGN PATENT DOCUMENTS

| | | | |
|---|---|---|---|
| JP | 60189575 A | * | 9/1985 |

OTHER PUBLICATIONS

Tamar Frankel, Securitization, Structured Financing, Financial Asset Pools, and Asset-Backed Securities, 1991, Little, Brown, pp. 3-8, and 37-38.*

Structured Finance Research & Commentary, "Asset-Backed Commercial Paper: Understanding the Risks", Moody's Investors Services,(Apr. 1993).

Structured Finance, Special Report, "Health Care Receivables Securitization: An Outline of The Issues", Moody's Investors Service,(Oct. 1993).

Summit Funding Corp., Private Placement Memorandum for $30 Million, Merrill Lynch & Co.,(Apr. 30, 1993).

"Asset-Backed Commercial Paper", Discussion Memorandum from Lehman Brothers, (Dec. 7, 1993).

"Selected Asset-Backed Commercial Paper Programs", Merrill Lynch, (Sep. 1993).

"the Hearts Program" For the Sale of Healthcare Accounts Receivable, Lehman Brothers.

Crockett, S..P., "Clinton Plan May Spur Health Care Securitizations", Standard & Poor's Credit Comment (Reprint) p. 1-3, (Aug. 1993).

Crockett, S.., "Securitizing Health-Care Receivables", Standard & Poor's Credit Week, p. 1-16, (Oct. 1994).

Humphreys, P..,"Securitization of Health Care Receivables", Annual New York Conference on Structured Finance, (Oct. 1991).

* cited by examiner

| Data Categories | Sample Data Fields |
| --- | --- |
| Patient | Name, Address, Age, Sex, Marital Status, Race |
| Account Number | |
| Admissions Date | |
| Discharge Date | |
| Statement Date | |
| Billing Instructions | Responsible party for Patient's bills |
| Remittance Instructions | Payor's Name and Address |
| Payor Subscriber ID | |
| Policy Number | |
| Professional Relationship, if services performed at a hospital/outpatient clinic | In House Staff vs Outside Specialist |
| Physician | Name and Address |
| Surgeon | Name and Address |
| Radiologist | Name and Address |
| Pathologist | Name and Address |
| Anesthesiologist | Name and Address |
| Diagnosis at Time of Admission | |
| Diagnosis at Time of Discharge | |

FIG. 12A

| Description of Service Procedure | Date of Service | Units | Total Charges | Amount Paid | Settlement Date |
|---|---|---|---|---|---|
| Pharmacy | | | | | |
| Supplies | | | | | |
| Lab/Pathology | | | | | |
| Radiology | | | | | |
| Therapy | | | | | |
| Emergency Room | | | | | |
| Room & Board | | | | | |
| Equipment Rental | | | | | |
| Miscellaneous | | | | | |

FIG. 12B

| Data Field | Data Definition |
|---|---|
| Provider ID | Field Identifying Provider |
| Patient ID | Field That Uniquely Identifies Patient |
| Payor ID | Field Identifying Claim Payor |
| Claim Number | Field Identifying Claim |
| Diagnostic/Procedural Code | Field Identifying Patient's Illness and Treatment |
| Physician | Field Identifying Physician Treating Patient |
| Admission Date | |
| Discharge Date | |
| Date Billed | Date Claim Sent to Payor |
| Amount Billed | Amount Charged for Services |
| Date Paid | Date Payor makes Payment on Claim |
| Amount Paid | Amount Paid for Treatment |
| Usual & Customary Reduction | Amount of Claim Written-off to Reflect Charging Pattern in Area |
| Contractual Reduction | Amount of Claim Disallowed because of Payment Contracts Between Provider and Payor |
| Amount Written-off | Amount of Claim Provider Charges off as Uncollectible |
| Claim Status | System Field for Identifying if Claim is New, being Updated, or being Closed |

FIG. 17

| Data Field | Data Definition |
|---|---|
| Expected Collection | Equals:<br>Amount Billed * Average Collection Rate for Payor from Prior Performance Statistics Table |
| Amount Advanced | Equals:<br>Expected Collection * Contractual Advance Rate from Advance Rate Table |
| Expected Uncollectible | Equals:<br>Amount Billed - Expected Collection |
| Equity | Equals:<br>Expected Collection - Amount Advanced - Expected Uncollectible |

FIG. 22

| Data Table in Master File from Seller | Data in Table |
|---|---|
| Prior Perfomance Statistics Table | Average, Standard Deviation, Sum of all Collection Rates, Sum of All Collection Rates Squared, Count of Number of Accounts Receivable in Statistical Analysis |
| Payor Effectiveness Table | Payor Effectiveness Index |
| New Daily Pool Table | Date Billed, Amount Billed, Amount Advanced, Expected Uncollectible, Expected Collections, Equity |
| Compliance Table | Total Concentration Disallowance |
| Expected Collection Histogram Table | Days from Billing, Expected Collection by Days from Billing |
| Changes to Existing Daily Pools Table | Date Billed, Amount Paid, Realized Uncollectible |
| Daily Payor Collection Table | Total Amount Paid by Payor, Total Amount Billed by Payor |
| Collection Performance Tracking Table | Difference between Expected and Actual Collections by Day from Billing |
| Current Performance Statistics | Average, Standard Deviation, Sum of all Collection Rates, Sum of All Collection Rates Squared, Count of Number of Accounts Receivable in Statistical Analysis |

FIG. 23A

| Data Table in Master File from SPE | Data in Table |
|---|---|
| Daily Collection Table | Amount Received into the SPE Bank Account for each Seller by Payor |
| Daily Advances Table | Amount Advanced made to each Seller |
| Daily Interest Expense Table | Interest Charges made to each Seller |
| Daily Third Party Fee Table | Third Party Fees Charged against each Seller |
| Daily Cash Settlement Table | Amount of Cash and Receivables released to Seller in Excess of Advances |

FIG. 23B

| Data Field | Data Definition |
| --- | --- |
| Conduit ID | This Field links the Record to a Database Identifying individual SPEs |
| Provider ID | This Field links the Record to a Database Indentifying Individual Providers |
| Payor ID | This Field links the Record to a Database Identifying Individual Payors |
| Advance Date | Date on which Commercial Paper proceeds are initially Advanced to Provider |
| Advance Amount | The Dollar amount advanced to the Provider |
| Date Paid | Date on which SPE receives Payments from individual Payors |
| Amount Paid | Amount of Payment received by SPE from each individual Payor |
| Third Party Fees | Amount charged to each Provider over a defined time period by the Financial Intermediaries associated with the Commercial Paper Program |
| Interest Expense | The Interest Expense charged to each Provider on the Advances made to the Provider |
| Settlement Payments | Payments made by the SPE to the Provider to transfer Cash Balances and Uncollected Receivables |

FIG. 28

| Data Field | Definition |
|---|---|
| Name | Organization Name |
| Contact/Title | Name of Contact Person and Title |
| Street Address | |
| City | |
| State | |
| Zip | |
| Work Phone/Fax | |
| Notes | Summary of all conversations with Contact Person |

FIG. 29

| Data Field | Definition |
|---|---|
| Payor ID | Name of Payor |
| Rating Date | Most recent date that claims paying ability of Payor was rated by independent Rating Agency |
| Rating Agency | Name of Rating Agency |
| Payor Type | Government, Private Insurer, HMO |
| Credit Rating | Rating reported by Rating Agencies |

FIG. 31

| Data Field | Data Definition |
|---|---|
| Ticket Number | CUSIP number used to identify specific Commercial Paper |
| Trade Date | Date Commercial Paper Sold |
| Settlement Date | Date cash proceeds received by Commercial Paper Seller |
| Maturity Date | Date Commercial Paper matures and principal and interest repaid |
| Par Amount | |
| Discount | Difference between the Par Amount of the Commercial Paper and the cash proceeds at settlement |
| Discount Rate | Usually quoted by broker, but can be calculated as follows: (discount/par amount)*(360/(maturity date-settlement date)) |
| Price | Equals: par amount*(1-((discount rate*(maturity date-settlement date))/360)) |
| Yield | Equals: (365*discount rate)/(360-discount rate*(maturity date-settlement date)) |
| Interest at Maturity | Equals: discount rate*par amount*((maturity date-settlement date)/360) |

FIG. 33A

| Data Field | Data Definition |
| --- | --- |
| Principal | Equals:<br>Par amount-interest at maturity |
| Daily Interest | Equals:<br>interest at maturity/(maturity date-settlement date) |
| Fed Composite Rates | This field is used for recording the commercial paper rates at different maturities the the Federal Reserve publishes in its H.15 Report |
| Commercial Paper Seller ID | This field links the commercial paper ticket to an information database on the commercial paper sellers |
| Trader ID | This field identifies the internal person who talked with the commercial paper seller |
| Conduit ID | This field identifies which SPE the commercial paper was issued for |
| Wire Instructions | This field tells which bank will clear the commercial paper transaction both for advancing cash and for returning principal and interest |

FIG. 33B

| Field Name | Financial Statement |
|---|---|
| Cash | Balance Sheet |
| Accounts Receivable | Balance Sheet |
| Bad Debt (Expected Uncollectible) | Balance Sheet |
| Bad Debt (Realized Uncollectible) | Balance Sheet |
| Interest Payable | Balance Sheet |
| Fee Payable | Balance Sheet |
| Advances Payable | Balance Sheet |
| Equity (beginning) | Balance Sheet |
| Retain Earnings | Balance Sheet |
| Interest Expense | Income Statement |
| Fee Expense | Income Statement |
| Net Income (Loss) | Income Statement |
| Amount Paid | Cash Flow Statement |

FIG. 41

| Input Source | Function | Output Table |
|---|---|---|
| Provider's Computer-based Accounting System | Capturing Claims Data | Archive Table<br>Recently Collected Table<br>Current Financial Table<br>Current Clinical Table |
| Archive Table | Statistical Analysis of Provider's Collection Experience to Determine Net Collectible Value | Prior Performance Statistics Table |
| Archive Table | Statistical Analysis of Provider's Collection Experience to Determine Collection Histograms | Collection Histogram Table |
| Prior Performance Statistics Table and Collection Histogram Table | Constructing Payor Effectiveness Index | Payor Effectiveness Table |
| Central Location Computer Download | Providing Commercial Paper Program Contract Information | Advance Rate Table<br>Payor Limit Table |
| Initial batch from Current Financial Table then from Provider's Accounting System<br>Advance Rate Table | Creating Trackable Periodic Units (daily pools) | New Daily Pool Table |
| Current Financial Table<br>Payor Limit Table | Calculating Compliance with Payor Limits | Compliance Table |

FIG. 52A

| Input Source | Function | Output Table |
|---|---|---|
| New Daily Pool Table and Collection Histogram Table | Projecting Daily Collections for Trackable Periodic Units | Expected Collection Histogram Table |
| Current Financial Table | Summarizing Changes to Existing Pools | Changes to Existing Daily Pools Table |
| Current Financial Table | Tracking Total Amount Paid by Payor | Daily Payor Collection Table |
| Current Financial Table and Expected Collection Histogram Table | Comparing Actual to Expected Collections | Collection Performance Tracking Table |
| Recently Collected Table | Statistical Analysis of Provider's Collection Experience Since Advance Rates Established | Current Performance Statistics Table |
| Archive Table Recently Collected Table | Analyzing Revenue by Product Line (Diagnosis or Service) | Revenue Analysis Table |
| Collection Histogram Table | Comparing Payor Performance by Speed of Payment | Collection Time Table |
| Central Location Computer | Reporting Information to Provider | Reconciliation Table Provider Income Statement Table Provider Balance Sheet Table Provider Cash Flow Table Peer Group Table Statistics Comparison Table |

FIG. 52B

| Input Source | Function | Output Table |
|---|---|---|
| SPE's Operating Agent Computer-based Accounting System | Capture Commercial Paper Program Data | Daily Collection Table |
| | | Daily Advances Table |
| | | Daily Interest Expense Table |
| | | Daily Third Party Fee Table |
| | | Daily Cash Settlements Table |
| Central Location Computer | Reporting Information to SPE Operating Agent | Collection Performance Tracking Table |
| | | Reconciliation Table |
| | | Provider Concentration Table |
| | | Payor Exposure Table |
| | | Credit Scoring Table |
| | | Statistics Comparison Table |
| | | Payor Effectiveness Table |
| | | Compliance Table |

FIG. 53

| Input Source | Function | Output Table |
|---|---|---|
| Provider Sentinel | Capture Data from Computer at Provider's Location | Prior Performance Statistics Table |
| | | Collection Histogram Table |
| | | Payor Effectiveness Table |
| | | New Daily Pool Table |
| | | Compliance Table |
| | | Expected Collection Histogram Table |
| | | Changes to Existing Daily Pools Table |
| | | Daily Payor Collection Table |
| | | Collection Performance Tracking Table |
| | | Current Performance Statistics Table |
| SPE Sentinel | Capture Data from Computer at SPE's Location | Daily Collection Table |
| | | Daily Advances Table |
| | | Daily Interest Expense Table |
| | | Daily Third Party Fee Table |
| | | Daily Cash Settlements Table |
| Program Participants | Contact Management System | SPE/Conduit Table |
| | | Providers Table |
| | | Commercial Paper Dealer Table |
| | | Payors Table |

FIG. 54A

| Input Source | Function | Output Table |
|---|---|---|
| Rating Agencies | Tracking Claims Paying Ability of Payors | Payor Credit Table |
| Contract Between SPE and Provider | Tracking Terms Under Which Provider Participates in Commercial Paper Program | Advance Rates Table<br>Third Party Fee Table<br>Payor Limit Table |
| Commercial Paper Dealer | Capture Data on Commercial Paper Issuance | Commercial Paper Table<br>Composite Rate Table |
| Commercial Paper Table | Calculating Daily Interest Expense for each SPE | Detail based Daily Interest Expense Table |
| Third Party Fee Table<br>Balance Sheet Table | Calculating Daily Third Party Fee Expense for each SPE | Detail based Daily Third Party Fee Table |
| New Daily Pool Table<br>Daily Advances Table | Reconcile SPE and Provider Advance Amounts | Reconciliation Table |
| Daily Payor Collection Table<br>Daily Collection Table | Reconcile SPE and Provider Amounts Collected | Reconciliation Table |
| Detail based Daily Interest Expense Table<br>Daily Interest Expense Table | Reconcile SPE reported and Commercial Paper Detail Interest Expense | Reconciliation Table |
| Detail based Daily Third Party Fee Table<br>Daily Third Party Fee Table | Reconcile SPE reported and Detai based Third Party Fee | Reconciliation Table |
| New Daily Pool Table | Entering Initial Pool Balances | Balance Sheet Table |
| Balance Sheet Table<br>Detail based Daily Interest Expense Table | Calculating Daily Interest Expense for Each Pool | Income Statement Table |
| Balance Sheet Table<br>Third Party Fee Table | Calculating Daily Third Party Fee Expense for Each Pool | Income Statement Table |

FIG. 54B

| Input Source | Function | Output Table |
|---|---|---|
| New Daily Pool Table<br>Balance Sheet Table<br>Changes in Existing Pools Table | Updating Balance in Accounts Receivable and Bad Debt for Collections and Realized Uncollectibles | Balance Sheet Table |
| New Daily Pool Table<br>Balance Sheet Table<br>Income Statement Table<br>Changes in Existing Pools Table | Updating Balance in Interest Payable, Fees Payable and Advances Payable for Daily Interest Expense, Daily Fee Expense, Interest Paid, Fees Paid, Advances Paid | Cash Flow Statement Table<br><br>Balance Sheet Table |
| Income Statement Table<br>Balance Sheet Table<br>Cash Flow Statement Table | Reporting Provider Level Financial Statements | Provider Income Statement Table<br><br>Provider Balance Sheet Table<br><br>Provider Cash Flow Table |

FIG. 54C

| | | |
|---|---|---|
| Daily Cash Settlements Table<br>Provider Cash Flow Table<br>New Daily Pool Table | Reconciling SPE and Provider Cash Settlements | Reconciliation Table |
| Expected Collection Histogram Table<br>Collection Histogram Table<br>New Daily Pool Table<br>Commercial Paper Table | Updating Asset/Liability Management Reports | Asset/Liability Table |
| Balance Sheet Table | Calculating Provider Concentration Statistics | Provider Concentration Table |
| Compliance Table<br>Payor Credit Table | Calculating Payor Concentration Statistics | Payor Exposure Table |
| Payor Effectiveness Table<br>Payor Credit Table | Generating Credit Scoring Report | Credit Scoring Table |
| Prior Performance Statistics Table<br>Current Performance Statistics Table | Comparing Collection Statistics to Determine if Change in Advance Rates Should be Triggered | Statistics Comparison Table |
| Prior Performance Statistics Table | Comparing Collection Statistics Between Providers | Peer Group Table |

FIG. 54D

SYSTEM FOR INVOICE RECORD MANAGEMENT AND ASSET-BACKED COMMERCIAL PAPER PROGRAM MANAGEMENT

This application is a continuation of U.S. Ser. No. 09/514,807, filed Feb. 28, 2000 now abandoned, which is a continuation of U.S. Ser. No. 08/336,531, filed Nov. 9, 1994 now U.S. Pat. No. 6,073,104.

TECHNICAL FIELD OF THE INVENTION

The present invention pertains generally to information management systems and more particularly to information management systems for use in obtaining and storing invoice records and in using these records to facilitate the creation or issuance of commercial paper backed by the receivables of medical providers or other receivable sellers, or for other purposes.

BACKGROUND OF THE INVENTION

Asset-backed commercial paper programs (also known as "conduits") take illiquid assets and bundle these assets into a segregated pool against which highly liquid money-market instruments can be issued. The cash collected on the underlying assets in the pool is the source of repayment of principal and interest on these instruments. In these programs, the underlying assets are the receivables of business entities and the market instrument that is issued is commercial paper. Asset-backed commercial paper programs use a financial "vehicle" called a special purpose entity (SPE) to issue commercial paper. The program provides a service basically similar to that offered by a factoring company (also known as a "factor"), in that the SPE finances the receivables of corporate clients. In other respects, however, the SPE differs from a factoring company. Typically, a factor assumes the role of a credit department for its clients to evaluate the credit-worthiness of the client's customers. While it finances a client's receivables by purchasing them, the SPE does not perform a credit evaluation of each obligor associated with the receivables in the pool as a factor would, but relies instead on an actuarial review of the past performance of the client's portfolio of receivables. With an SPE, the corporate client usually performs the servicing function, whereas in a factoring arrangement, the factor generally services the receivables. Asset-backed commercial paper programs are ongoing activities. The SPE continually purchases new receivables and usually "rolls over" the outstanding commercial paper.

FIG. 1 shows the structure and cash flows of a conventional prior art paper program 10. Prior to acquiring the receivables, the program sponsor 26 reviews the receivables. The review covers the credit origination standards of the company 14 originating the receivables and current and historical quality and performance of this portfolio. The asset backed commercial paper program uses an SPE 12 to acquire legal title to receivables directly from a company 14 participating in the program To obtain finding, the SPE 12 issues commercial paper to an investment bank 16. The investment bank 16 sells the commercial paper to investors 18. The commercial paper is ultimately repaid by the SPE 12 from the cash flow of the underlying pools of receivables. The rating agencies require that the entire amount of outstanding commercial paper be covered by liquidity and credit enhancements before the program can receive the highest investment rating. These enhancements are provided by credit enhancer 20 and liquidity provider 22. Employees of the investment banking firm 16 generally own the equity of the SPE. The owner 24 of the SPE 12 receives dividends. A program sponsor 26 such as a bank receives a fee.

Health care receivables differ in several important ways from other types of receivables that have been securitized to date. Health care providers, by delivering various forms of medical services, are the originators of health care receivables (also known as medical claims). The bill for the services rendered may be payable entirely by the patient, entirely by some form of insurance, or partially by the patient and partially by insurance. The insurance payors and the patient are the obligors on the receivable. The insured portion of a health care receivable may be payable by a government program (such as Medicare), a Blue Cross/Blue Shield insurance company, a private insurance company, or a Health Maintenance Organization (HMO).

Unlike most other types of receivables, the face amount of the medical claim may have limited relevance to the amount the health care provider can reasonably expect to collect. The reimbursement procedures for medical services are complicated. For example, Medicare might be willing to pay only a fraction of the amount billed based either on their system of diagnostic-related groups (DRGs), the use of a resource-based value scale (RBVs), or on allowable costs incurred. Similarly, Blue Cross/Blue Shield or a private insurance company might limit the amount paid to a percentage of the provider's fees and charges, or an estimate of the reasonable and customary charge for the procedure in the locality in which the medical service was rendered. Finally, an HMO may pay on a per diem rate or on a fixed-fee-per-person basis (capitated payment).

Claims paid by Medicare are also subject to the requirement that they are directly payable to the health care provider. A consequence of the direct payment requirement is that Medicare payments paid to a bankrupt provider/seller might be trapped by the Bankruptcy Code's automatic stay. This risk could be reduced in a commercial paper program by making the provider set up a "bankruptcy-remote" subsidiary through which all Medicare claims are billed. The conduit can then lend money to the bankruptcy-remote subsidiary and take a senior secured position against the subsidiary's assets.

As described below, the present invention provides an information system to facilitate securitization of medical receivables. The invention is applicable to other types of receivables as well.

SUMMARY OF THE INVENTION

According to one embodiment, the present invention provides a system for processing electronic medical claim records originating in one or more health care provider accounting systems, with each accounting system executing at least in part on a provider computer system at a provider location. Each claim record includes (i) a date field specifying a date for the claim, and (ii) a financial data portion specifying a fee charged for services rendered to a patient. The system includes means for searching the claim records and identifying records that have a date specified in the date field that is within a predetermined period. The system further includes means for creating an electronic periodic pool record corresponding to all of the claim records within the period. The system also includes means for recording a pool advance amount in a field of the electronic periodic pool record representing an amount to be advanced against a value of the periodic pool of claims.

According to another embodiment of the present invention, there is provided a system for processing electronic invoice records originating in one or more goods or services provider accounting systems wherein each accounting system executes at least in part on a provider computer system at a provider location. Each record includes (i) a date field specifying a date for the invoice, and (ii) a financial data portion specifying a fee charged for goods or services rendered to a customer. The system includes means for searching the invoice records and identifying records that have a date within a desired range to identify a pool of invoice records representing a corresponding pool of invoices, and means for creating an electronic periodic pool record corresponding to the pool of invoice records. The system further includes means for recording a pool advance amount in the electronic periodic pool record representing an amount to be advanced against a value of the pool of invoices.

According to various other embodiments of the invention there is provided a central processing system receiving claim or invoice records and processing those records for transmittal to a commercial paper conduit, for reconciling the records of the provider and the conduit, and for generating various reports revealing important characteristics of the performance of asset pools and the payors on those pools.

BRIEF DESCRIPTION OF THE DRAWINGS

FIGS. 12A and 12B illustrate the fields of a typical medical claim record in a provider's accounting system.

FIG. 17 illustrates the data fields of the current financial and recently collected tables.

FIG. 22 illustrates the calculated fields of a daily pool record.

FIGS. 23A and 23B illustrate a master file to be transferred from a provider sentinel to the computer system at the central location.

FIG. 28 illustrates the data downloaded from a SPE computer system.

FIG. 29 illustrates the data fields maintained for the contact management system.

FIG. 31 illustrates the fields of the payor credit table.

FIGS. 33A and 33B illustrate the fields of a record in the trade ticket table.

FIG. 41 illustrates the fields to be tracked for a balance sheet for a pool.

FIGS. 52A and 52B illustrate the input data, functions and output data for the system 30 at the seller's location.

FIG. 53 illustrates the input data, functions and output data for the system 30 at the SPE's location.

FIGS. 54A, 54B, 54C and 54D illustrate the input data, functions and output data for the system 30 at the central location.

DETAILED DESCRIPTION OF THE INVENTION

Figure 1:
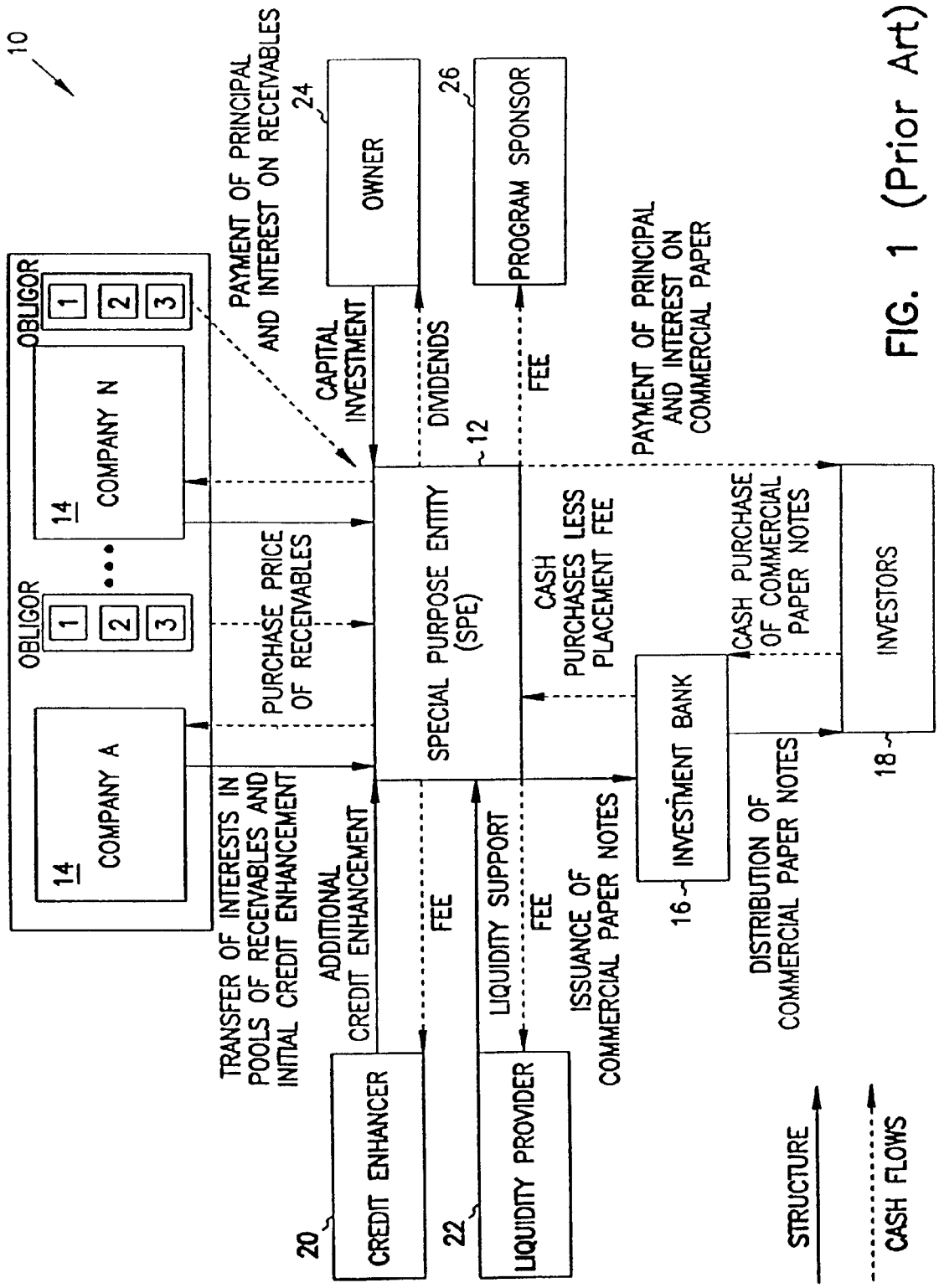
FIG. 1 illustrates a prior-art commercial paper program.
Figure 2:
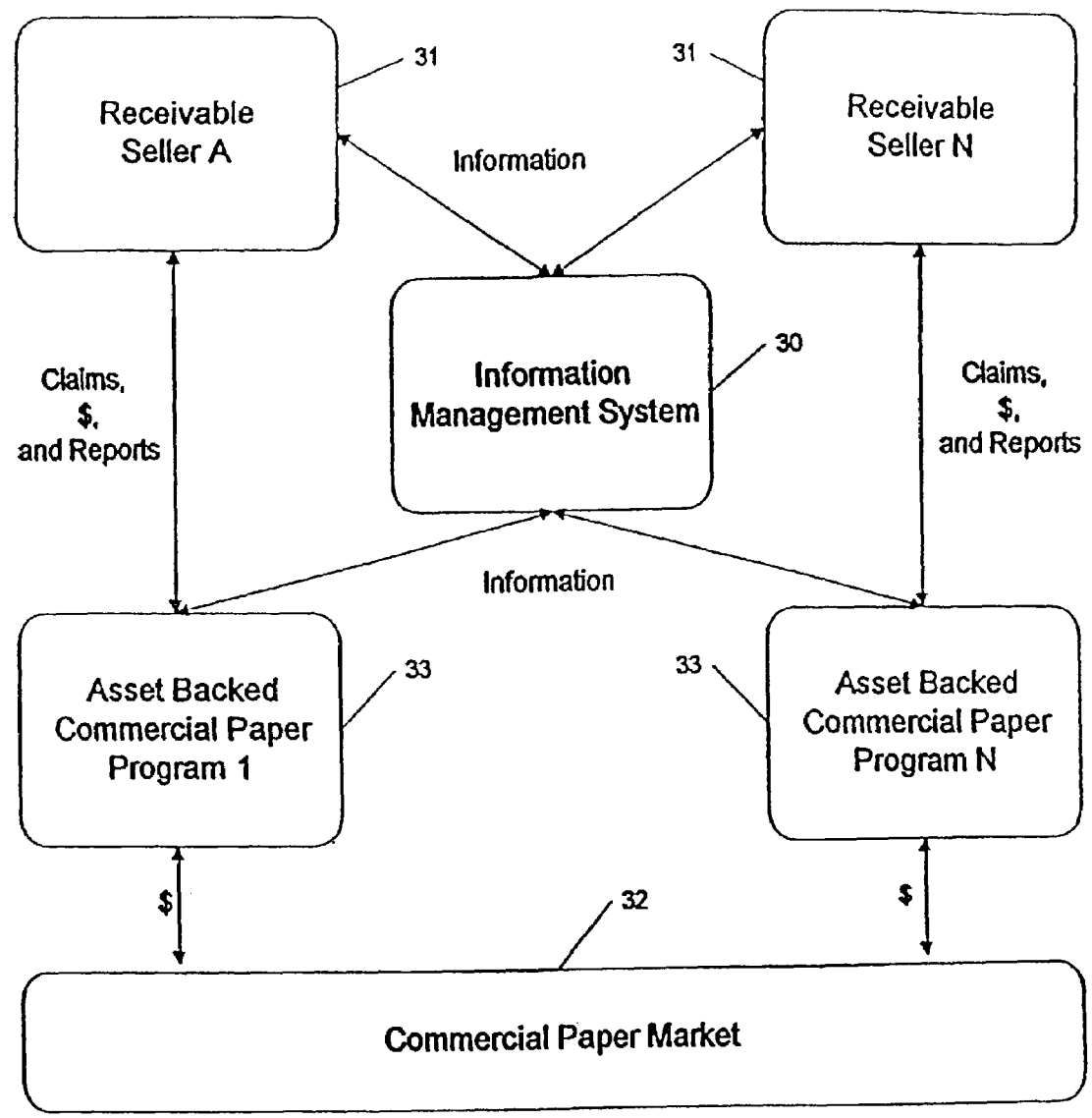
FIG. 2 illustrates an overview of a first exemplary embodiment of the information management system of the present invention.
Figure 3:
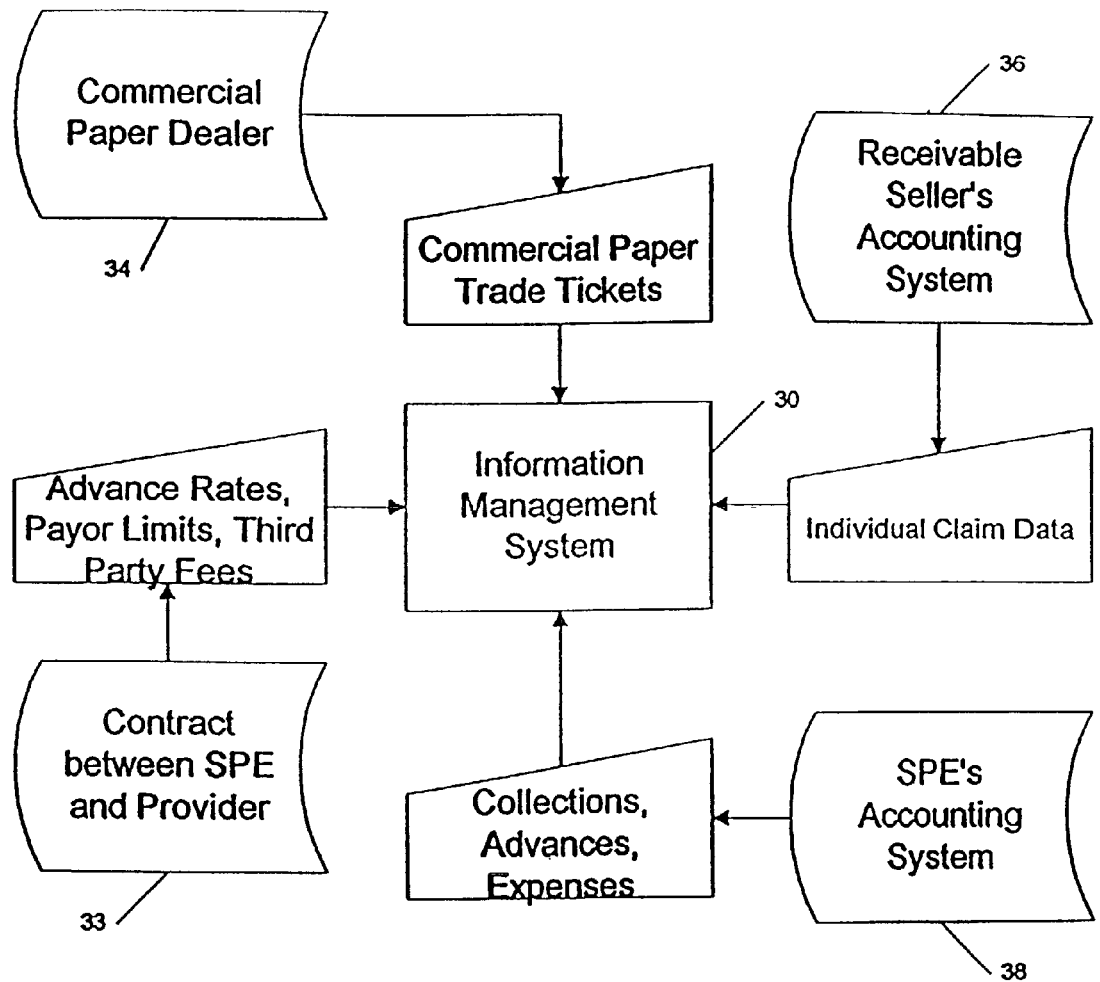
FIG. 3 is a simplified illustration of the sources of information used by the information management system 30 of the present invention.
Figure 4:
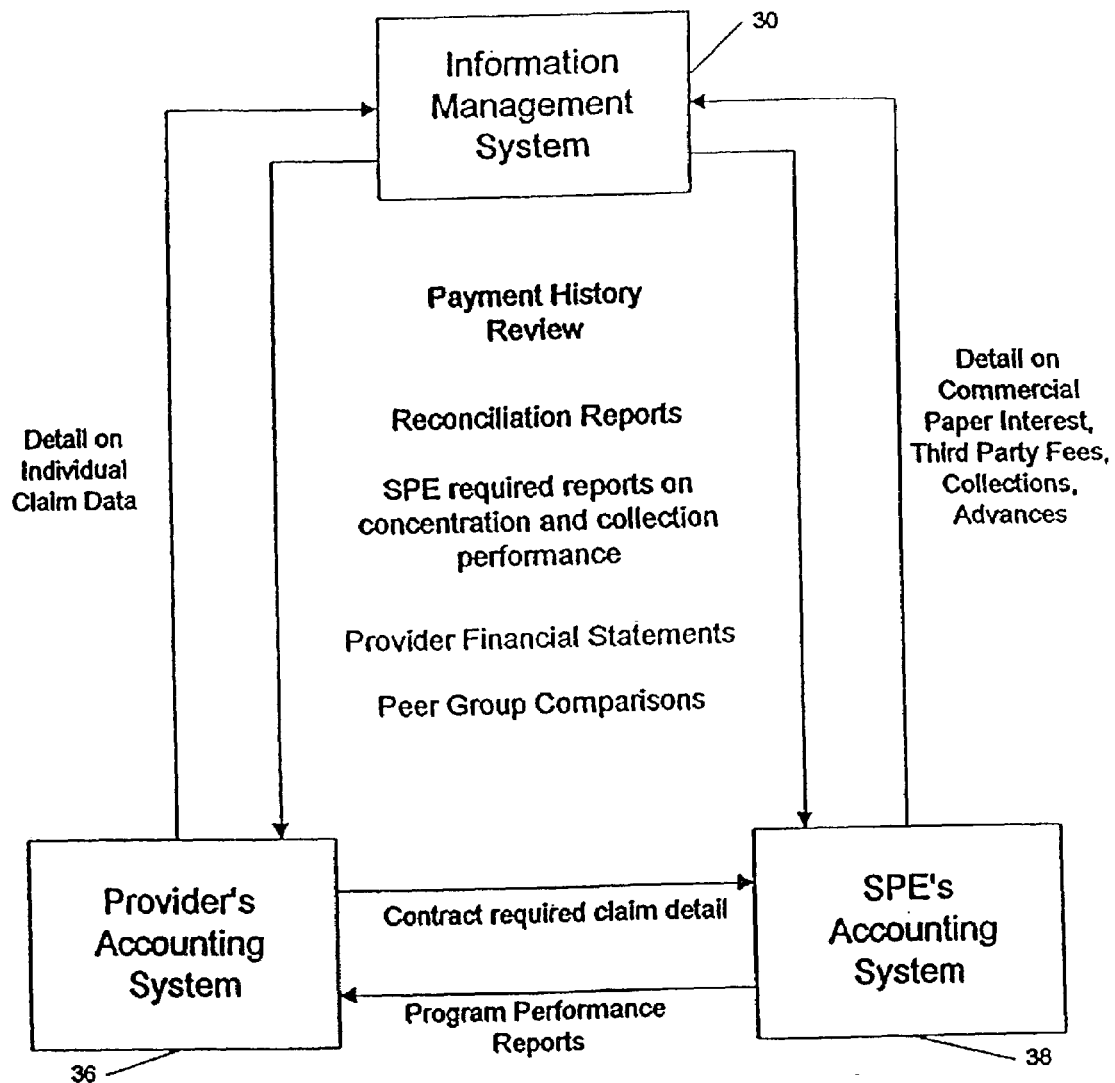
FIG. 4 is a simplified diagram showing information flow in the system of the present invention.

In the following detailed description of the preferred embodiment, reference is made to the accompanying drawings which form a part hereof and in which is shown, by way of illustration, an exemplary embodiment in which the invention may be practiced. This embodiment is described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims. As used herein, the terms "file" and "table" are equivalent.

Overview

As shown in FIGS. 2, 3, 4, and 5, the present invention provides an information management system 30 that supports access of a healthcare provider or other receivable seller 31 to the commercial paper market 32 through "selling" their claims to asset-backed commercial paper programs 33 (also known as "conduits"). The present invention captures, manipulates, and reports all of the data necessary to support the receivable seller's participation in an asset backed commercial paper program.

The information management system captures and manipulates data from four sources: the receivable seller's accounting system 36, the SPE's operating agent's accounting system 38, the SPE's commercial paper dealer 34, and the contract 33 between the SPE and the receivable seller 31. The information management system generates reports for the receivable seller and the SPE's operating agent.

Data flows into the system in three places: at the receivable seller's location 40, at the SPE's operating agent location 60 and at a central location 50. Historic and current claims billing and payment data is obtained from claim records on the receivable seller's accounting system 36 (executing on the seller's mainframe or other computing system 46) at the seller's location 40. Data on advances, interest expense, third party fee expense, collections, settlement payments and dividends is obtained from the SPE's accounting system 38 (executing on SPE's mainframe or other computing system 66) at the SPE's operating agent location 60. Commercial paper information including trade date, settlement date, maturity date, par amount and discount rate are obtained from the SPE's commercial paper dealer and stored at the central location 50. The contract 33 between the SPE and the receivable seller 31 provides data on advance rates against specific types of claims and financial intermediary fees. This data is input and updated at the central location 50 and downloaded to the seller's location 40.

The system processes the data in two places: at the receivable seller's location 40 and at the central location 50. At the receivable seller's place, the historical data is used to generate statistical data showing both the amount and timing of collections. This information is forwarded to the SPE's operating agent at location 60 where it is used to establish advance rates for the various payors of the receivable seller's claims. On an ongoing basis, the current claims data is divided into trackable periodic units so as to be able to reconcile advances, collections, interest expense, third party fees and cash settlements between programs 33 and receivable sellers 31. When a periodic unit is formed, expected collections on the claims in the unit are projected over time. As the claims in the unit are paid off, this information is also gathered. Realized collections are compared with expected collections to show the collection performance of each periodic unit. The realized collections are also used to generate statistical data showing the amount and timing of collections for comparison with the historical data. All of the periodic unit data is forwarded to the central location for further processing.

The computer system 51 at the central location 50 uses either the actual detail or the claims detail summarized in the periodic units to perform reconciliations with the data reported by the SPE, to prepare financial statements for the individual receivable sellers 31, to generate SPE required concentration and collection performance information and to produce comparisons between receivable sellers. The central location 50 reports periodically the results of the reconciliation, the financial statements, the receivable seller specific tracking information, and the peer comparisons to the receivable seller. The central location 50 also reports periodically the results of the reconciliation and the SPE required information to the SPE.

The information management system can handle claims from multiple receivable sellers and their corresponding accounting systems as well as multiple commercial paper programs.

First Exemplary Embodiment

As described in detail below, the first exemplary embodiment of the invention is adapted for providers of healthcare who wish to sell receivables into a commercial paper program. In this embodiment, the periodic units are daily. It shall be understood, however, that the system is readily adaptable to providers of other services or goods who have accounts receivables available to sell to a commercial paper program.

System Configuration Provider Location

Figure 5:
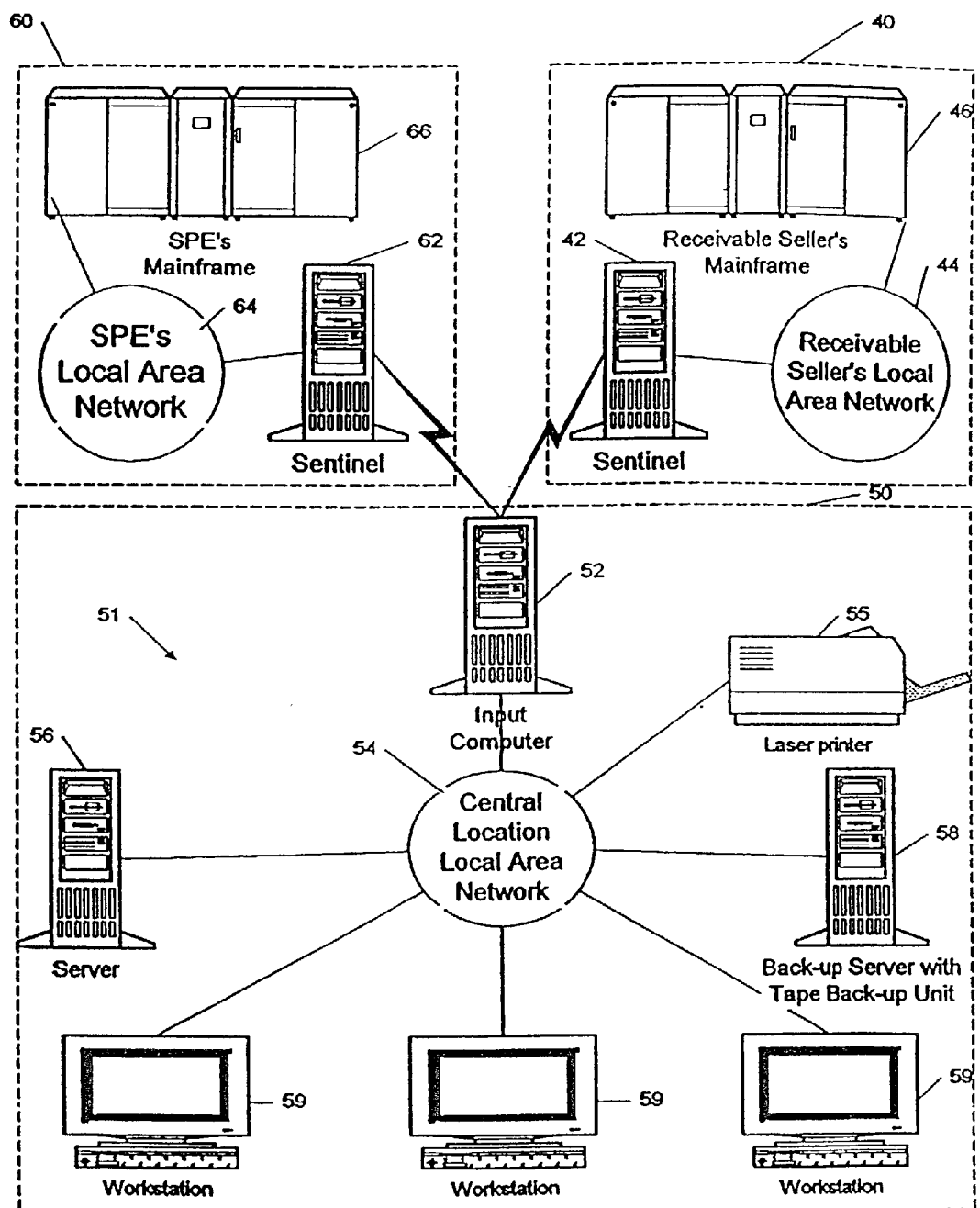
FIG. 5 illustrates the hardware configuration of the system of the present invention.

As shown in FIG. 5, which illustrates the first exemplary embodiment of system 30, the hardware configuration at each healthcare provider's location 40 includes a personal computer or workstation acting as a remote sentinel system 42. The currently preferred system 42 uses an Intel processor system, the "Microsoft Windows for Workgroups" operating environment, a database program comprising a runtime version of Microsoft's "Access" database program, Tools & Technologies' Data Junction program for capturing and translating data between various computer platforms, and International Software's Remote Office™ computer communication program Sentinel system 42 preferably has two one-gigabyte hard drives and an internal fax/modem. The second one-gigabyte hard drive mirrors the first drive and serves as a backup. The sentinel system 42 is connected to the provider's local area network 44, and can download claim records and other information directly from the providers mainframe or other computing facility 46, which executes the accounting system 36. The sentinel system 42 sends summary data to the central location 50.

Figure 6:
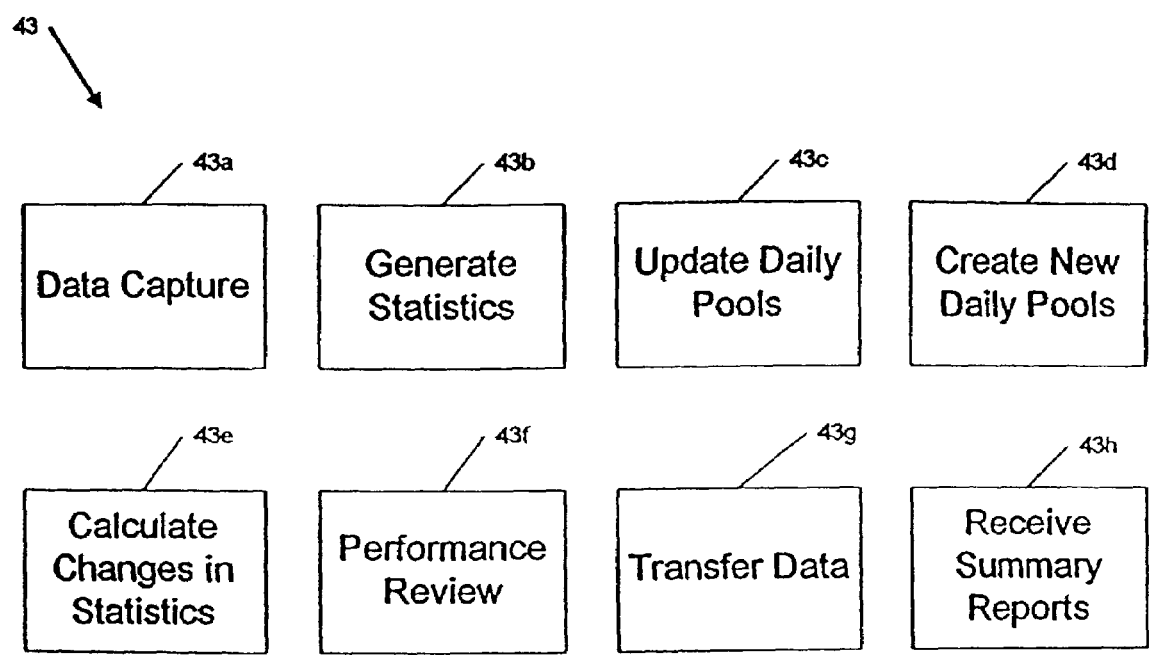
FIGS. 6 and 7 illustrate the software and data maintained on a receivable seller's sentinel system according to the present invention.
Figure 7:
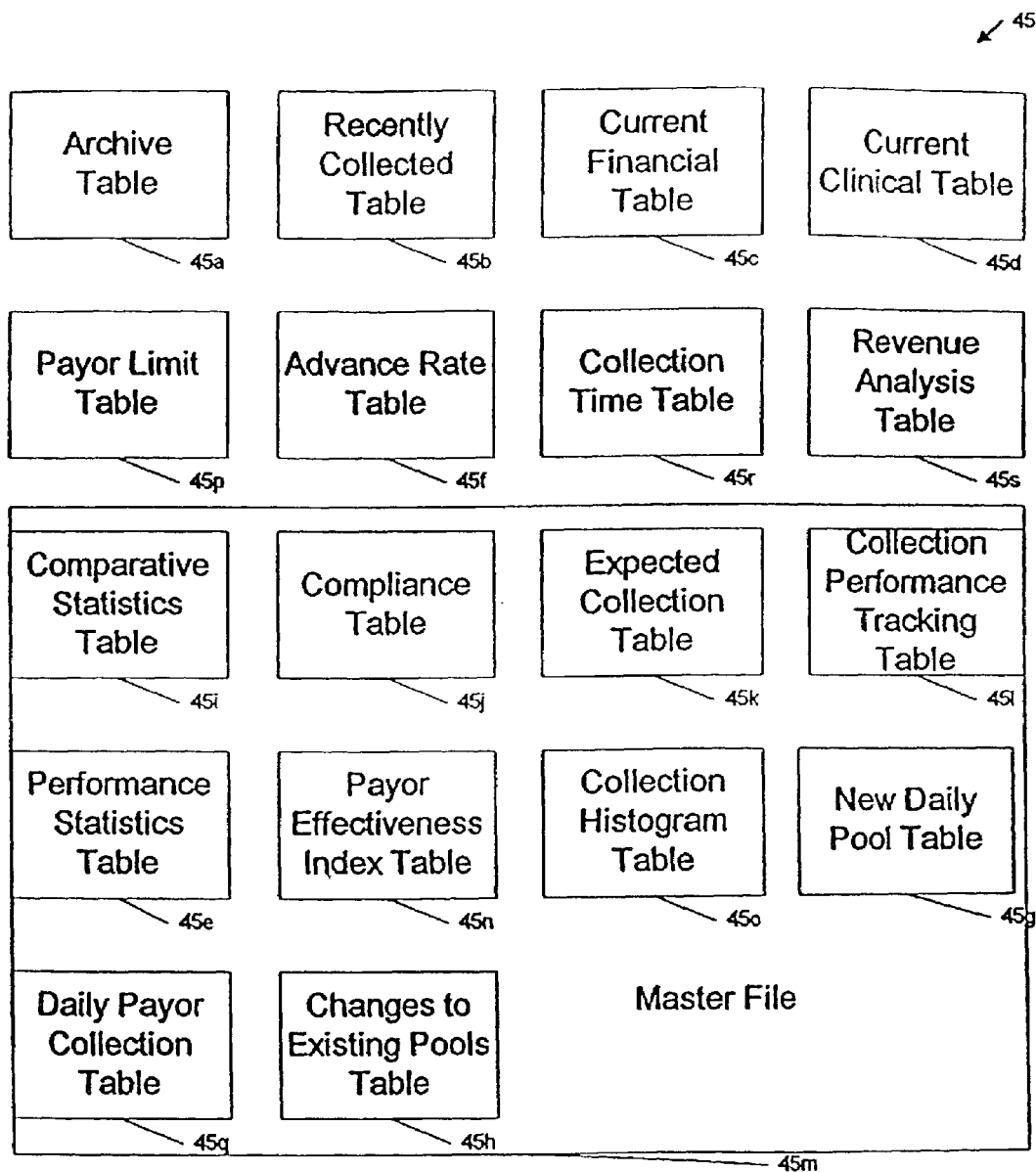

As illustrated in FIG. 6, the software 43 executing on the sentinel computer 42 at the provider location 40 performs a variety of functions: capturing data from the provider's accounting system (43a), generating statistical information (43b); consolidating and updating outstanding claims into daily pools (43c), creating pools from new claims submitted by the provider (43d); calculating statistics for use in determining whether the collections on outstanding and new claims have changed enough from the analysis on which the advance rates are based to merit a revision of the advance rates (43e); contrasting payor payment performance by timing of payment; analyzing revenue by service by payor (43*f*); and transmitting to and receiving from the central location 50 summary data and reports (43*g*). FIG. 7 illustrates the various tables and files of data 45 maintained in files on sentinel system 42, to be described in more detail below.

Although only one provider location 40 and SPE location 60 is shown in FIG. 5 for brevity, system 30 can accommodate and contemplates a plurality of either SPE or provider locations connected to the central location via sentinel systems. Furthermore, the same provider may supply information to the central location 50 from more than one location 40.

SPE cation The preferred system configuration also includes a personal computer or workstation acting as a remote sentinel 62 in each SPE location 60. This location 60 will typically be a bank which acts as the operating agent of the SPE. The sentinel system 62 preferably includes an Intel processor, the Microsoft "Windows for Workgroups" operating environment, a program comprising a runtime version of Microsoft's "Access" database program, the Data Junction™ data capture program from Tools & Technologies, Inc. of Texas, USA, and the Remote Office™ remote control communication program from International Software, Inc. of Minnesota USA. The sentinel system 62 preferably includes two five-hundred-megabyte hard drives and an internal fax/modem. The second hard drive mirrors the first drive and serves as a backup in case the first drive fails. The sentinel system 62 is interfaced to the bank's local area network 64 and can obtain information directly from the bank's mainframe or other computing facility 66. The sentinel sends summary data to central location 50, which processes this data and generates reports. Reports, including information generated at the provider, are transmitted back to the individual SPE's operating agent.

Figure 8:
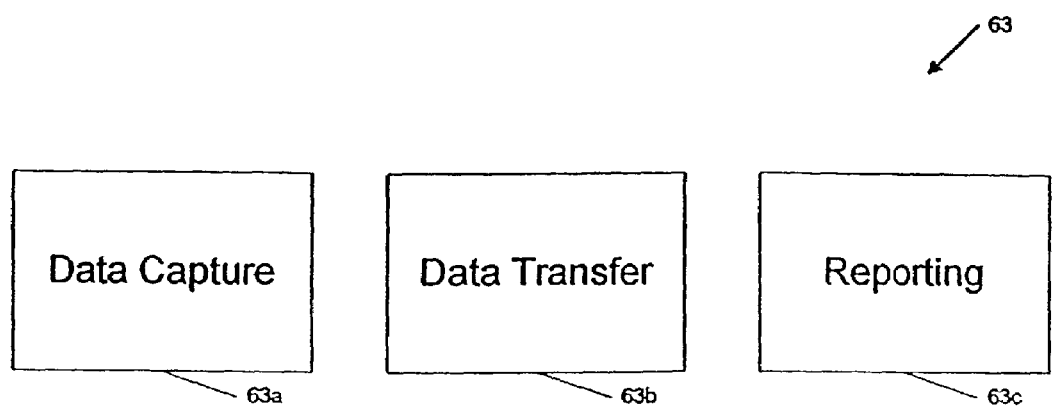
FIG. 8 illustrates the software maintained on an SPE's sentinel system according to the present invention.

As illustrated in FIG. 8, the software 63 executing on the sentinel computer 62 at the SPE location 60 performs a variety of functions: capturing and storing data from the SPE's accounting system (63*a*), transmitting to and receiving from the central location 50 summary data (63*b*); and reporting program information to the SPE (63*c*).

Central Location

The central location 50 processes data received from the sentinels 42 and 62 and generates all reports. The reports are transferred back to both the individual providers and the SPE's operating agents. Data from the commercial paper dealer and the contract are entered into the system 30 at the central location 50. The computer system 51 at central location 50 preferably has three types of computers. An input/output computer 52 is preferably an Intel processor, with the Microsoft "Windows for Workgroups" operating environment, and a database application developed using Microsoft's "Access" database program. In addition, it preferably has one five-hundred-megabyte hard drive, a fax/modem, a remote control communication software package, preferably International Software's Remote Office™, and a virus-screening package. During the time when the I/O computer 52 is communicating with other offsite computers, it is disconnected from the local area network 54. After the I/O computer 52 has received all of the incoming data, it transfers the data to primary file server 56 for processing. The primary file server 56 processes the data and transfers back reports to the computer 52 to transmit to the provider's sentinel system 42 or the SPE's sentinel system 62. Primary file server computer 56 preferably includes an Intel processor, the Microsoft "Windows for Workgroups" operating environment, a database program comprising a routine version of the Microsoft "Access" database program, and a statistics application developed using Microsoft's "Excel" spreadsheet program. It also has a one-gigabyte hard drive. A second file server 58 is provided to back-up the primary file server 56. It has the same configuration as the primary file server 56 with the addition of a tape backup unit, and receives the same information as the primary file server 56. A laser printer is connected to network 54. Finally, workstations 59 are provided, which preferably include an Intel processor, Microsoft "Windows for Workgroups" operating environment and the Microsoft "Office Suite" programs. Workstations 59 preferably include five-hundred-megabyte hard drives. Local area network 54 preferably utilizes the Novell network environment and is a token-ring configuration. Although only one provider location 40 and SPE location 60 are illustrated, the system may, and is contemplated to, include a plurality of locations 40 and 60 interfaced to I/O computer 52 through multiple corresponding sentinels 42 and 62.

Figure 9:
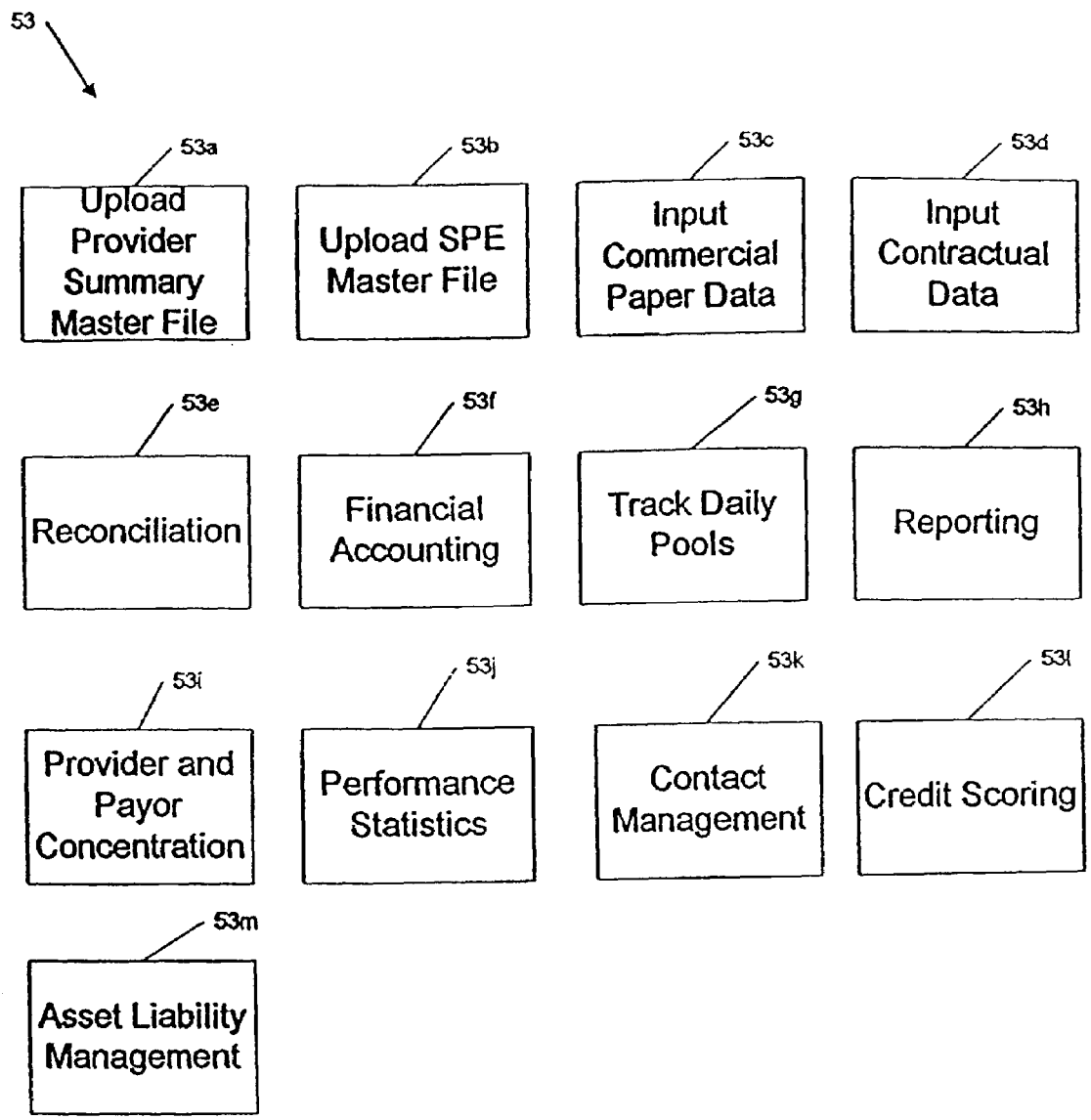
FIGS. 9 and 10 illustrate the software and data maintained on the computer system located at the central processing location.
Figure 10:
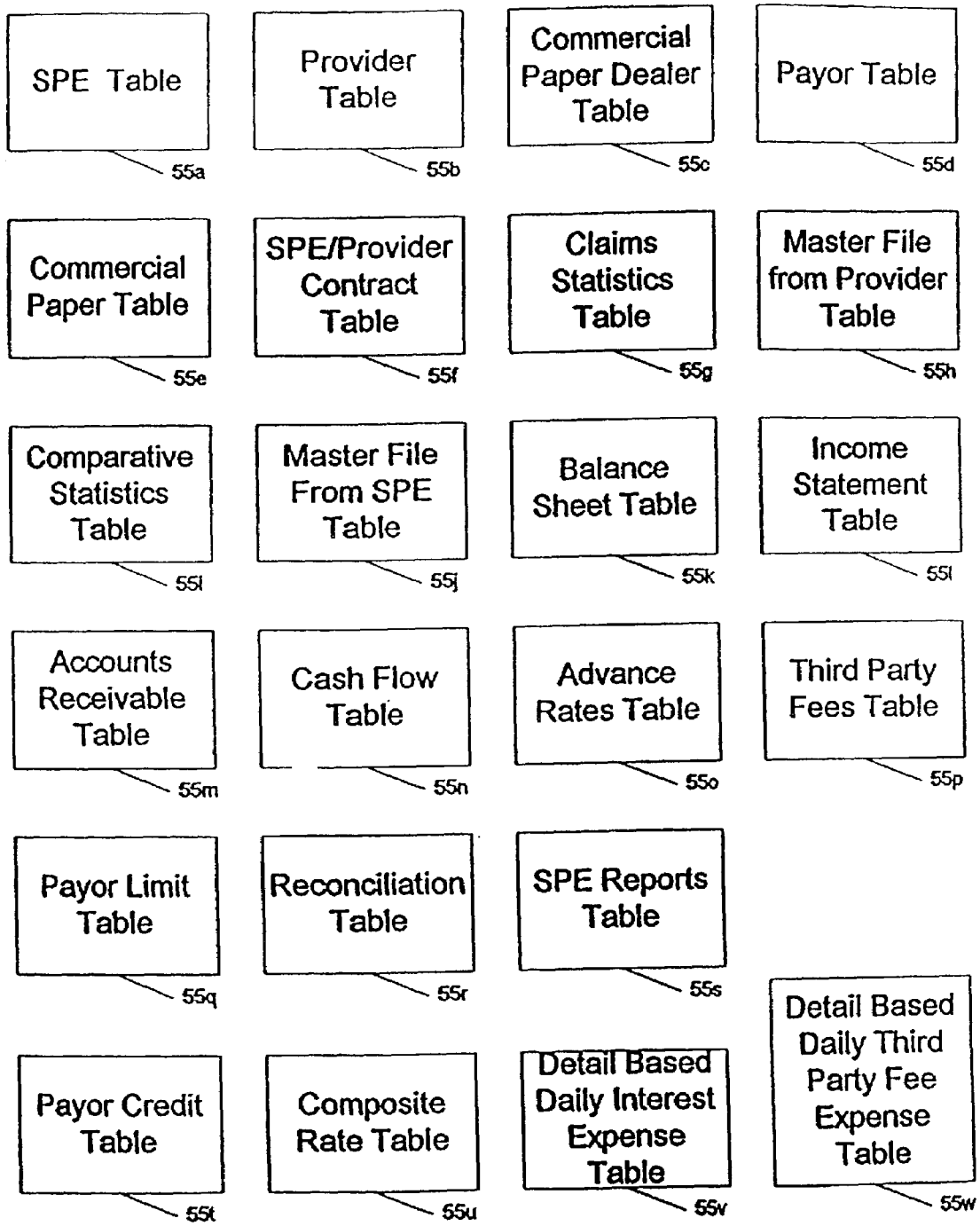

As illustrated in FIG. 9 and to be explained in more detail below, software 53 executing on the computer system 51 at the central location 50 has several functions: it receives the data from the provider and SPE sentinels 42 and 62 (53*a* and 53*b*); it captures the data from the SPE's commercial paper dealer (53*c*) and the contract between SPE and provider (53*d*); it reconciles all of the detail and summary level data (53*e*); it reports a credit scoring index based on each providers payor effectiveness index and the credit rating for the payor (531); it generates the financial accounting statements (53*f*) for the individual providers by tracking daily pools (53*g*); it creates asset/liability management reports to monitor and control interest rate and liquidity risk (53*m*); it reports financial statements to individual providers (53*h*) and concentration and tracking statistics to SPE's (53*i*); it calculates performance statistics (53*j*), and it includes a contact management system (53*k*). FIG. 10 illustrates various tables and files 55 maintained on the file serve 56 at the central location 50, to be described below.

Provider Sentinel Functions Capturing Claim Data

Figure 11:
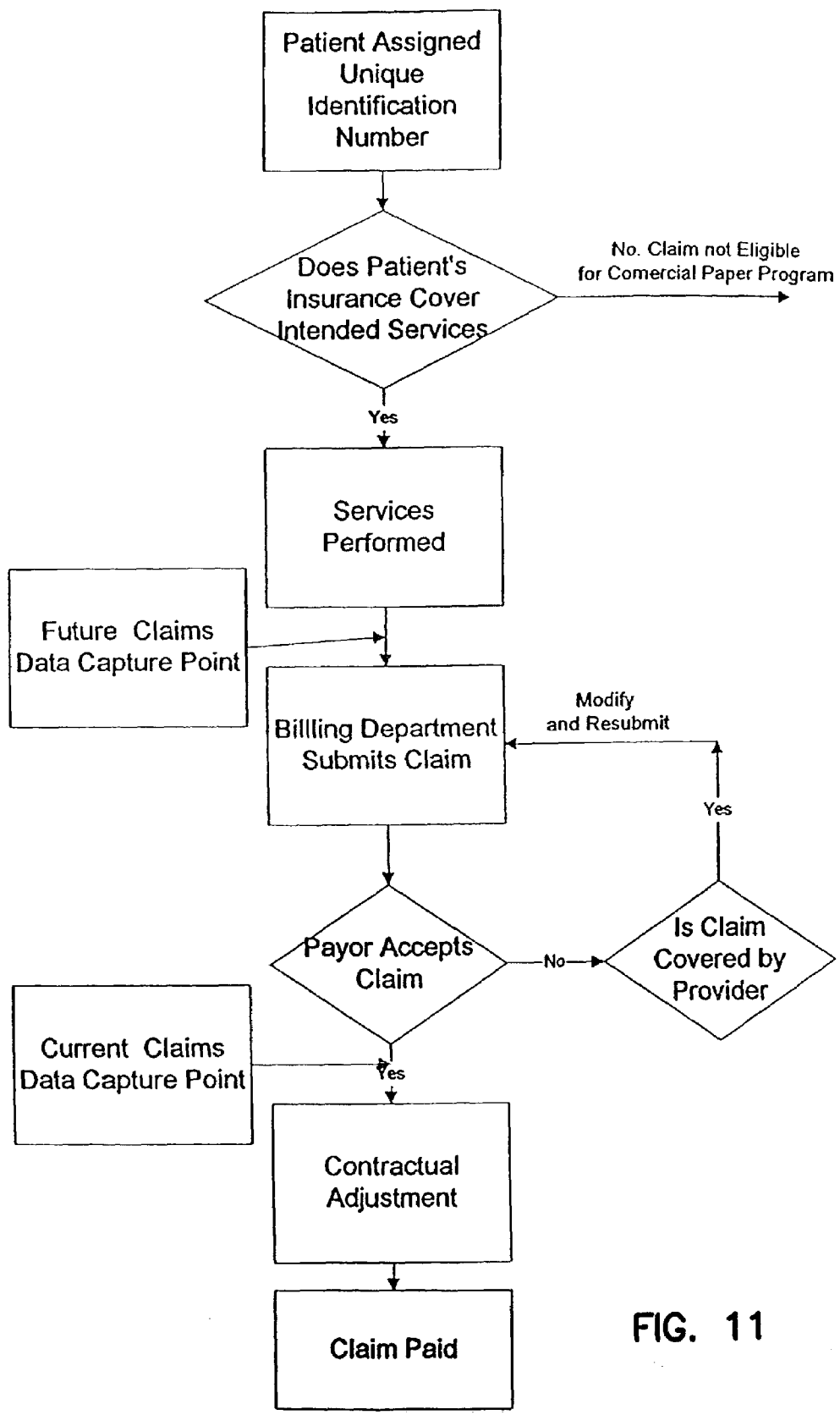
FIG. 11 illustrates the life cycle of a medical claim.

The first steps in implementing a commercial paper program, both in setting up the program and in running it on a day-to-day basis, is capturing claim data from the provider's accounting system 36. FIG. 11 shows the typical flow of a patient claim from origination through payment as experienced by the provider. The claim begins with the assignment of a unique identification number to the patient. The provider then verifies that the services to be performed are covered by the patient's insurance, and the services are performed. The billing department consolidates the charges for all services performed in the provider's accounting system and submits the claim to the payor. The payor accepts the claim or, depending on the quality of the provider's insurance verification process, rejects the claim outright citing contractual issues or rejects specific line items in the claim. If the claim is rejected, it goes back to the billing department where, if appropriate, it is modified for resubmission. After acceptance by the payor, the claim is then discounted for contractual adjustments, and paid. FIGS. 12A and 12B illustrate typical data fields found in electronic claims records stored or originating in a provider accounting system 36. Claim records exported from accounting system 36 to sentinel system 42 preferably include substantially all the date fields illustrated in FIGS. 12A and 12B.

Figure 13:
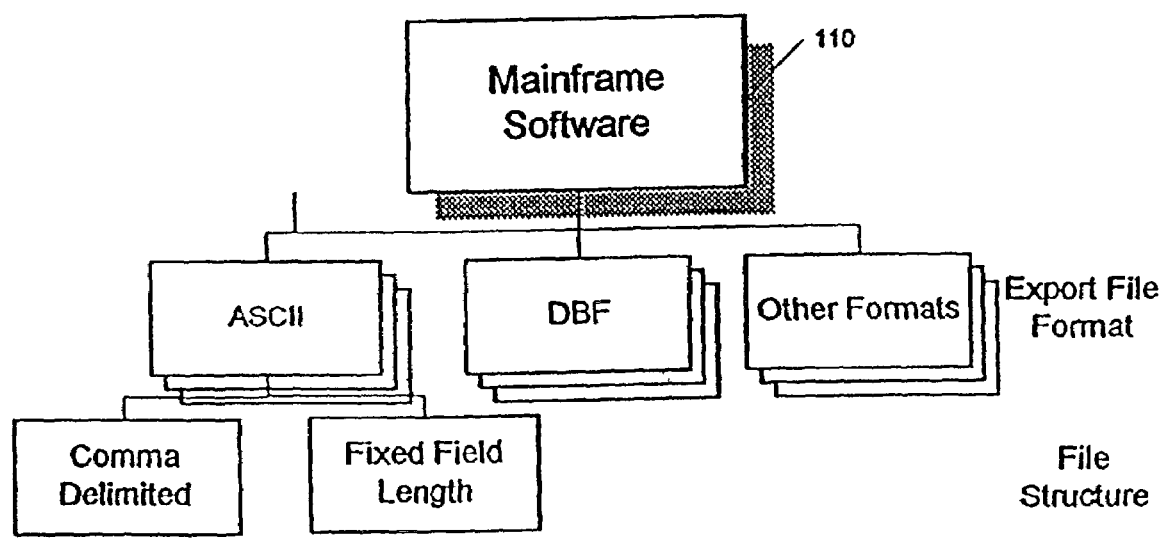
FIG. 13 illustrates the formats for export of data from a computer system.

FIG. 13 shows data structures for export files that can be used to export claim records or other information from the providers accounting system 36 across the local area network 44 to the sentinel computer 42. Mainframe software 110 (including, but not limited to, the accounting software executing on the mainframe) generates and manipulates these export files. Regardless of what export file language is used, the export file is accompanied by an export specification that defines what data items are in each field in the data file. The file is downloaded to the sentinel 42 over the network 44 where it is captured by the sentinel system 42 using the Tools & Technologies' Data Junction™ program. The same file exporting technique is used to export data from an SPE's mainframe 66. If a single provider tracks receivables at geographically separate locations, the system 30 employs sentinel systems 42 at each provider site 40.

Figure 14:
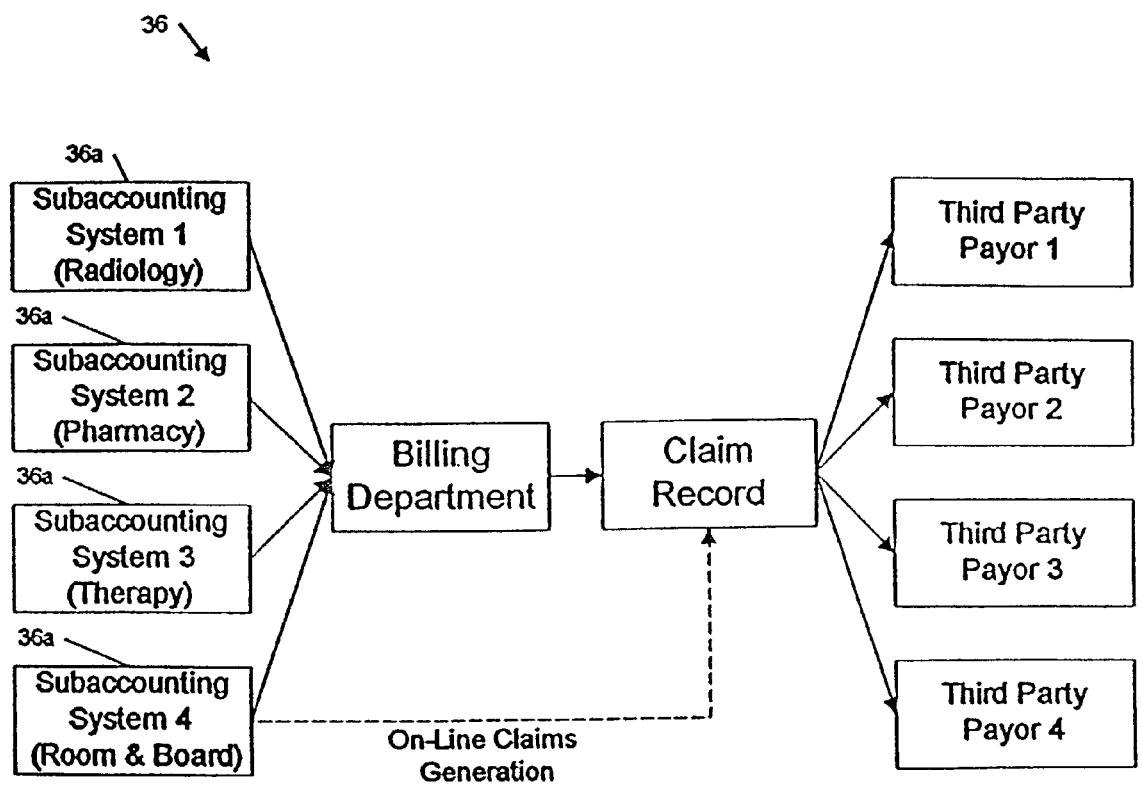
FIG. 14 illustrates the flow of claims through a provider's accounting system.

FIG. 14 depicts how data moves through a provider's accounting system. Data is initially input into the system through several sub-accounting systems (36a). Subsystems 36a each represent for example, a point of data input at the provider. For example, x-rays are charged for through the radiology sub-accounting system. Accounting system 36 aggregates all of the information for each patient off of the sub-accounting system 36a. This information is then stored in an electronic claim record on the computer and put onto the billing form appropriate for each third party payor involved with a specific patient. If the claim is not eligible for payment by an approved payor, the payor field in the claim record is set to "ineligible" or the like. There are two primary places in this flow of information through the accounting system to capture claim data for export by the provider's mainframe 46. First, the data can be extracted from the accounting system 36 in a batch mode. When the accounting system 36 is updated for new claims, payments on existing claims or other changes, the new or updated claims are flagged and the mainframe software 110 is programmed to both write this data to an export file and notify the sentinel computer system 42 of the update. The sentinel system 42 then reads the export file. Preferably, the export file is a standardized format so that all sentinels 42 receive the provider electronic claim recorded in the same format. The export data software of mainframe software 110 is thus configured to convert data from the provider's accounting system format to the standardized export format. Alternatively, the software on sentinel 42 can convert the exported records to a standardized format upon receipt of the export file.

Second, as an alternative embodiment, the mainframe software 110 generates an update to the export file every time an entry is made into one of the subaccounting systems 36a feeding data into the main accounting system 36. The sentinel computer 42 reads the update and generates a claim record. In initial installations of the information management system 30, it is preferred that it capture data that has been generated in a batch mode. As the SPE's gain experience handling medical receivables, there will be a greater inclination to finance the claims as they are being generated. When this occurs, the claims are, if desired, captured directly from the subaccounting systems 36a at the time they are created.

Downloading of Claim Data into Provider Sentinel

After the provider's mainframe software 110 has transmitted the claim data to the export file and the sentinel system 42 has read the export file in, the claim records received in the export file are used to update and create new records in claim data tables maintained on sentinel 42. Referring to FIG. 7, which shows the tables stored on sentinel 42, there are four tables which reflect this division: current financial table 45c, current clinical table 45d, recently collected table 45b and archive table 45a.

Figure 15:
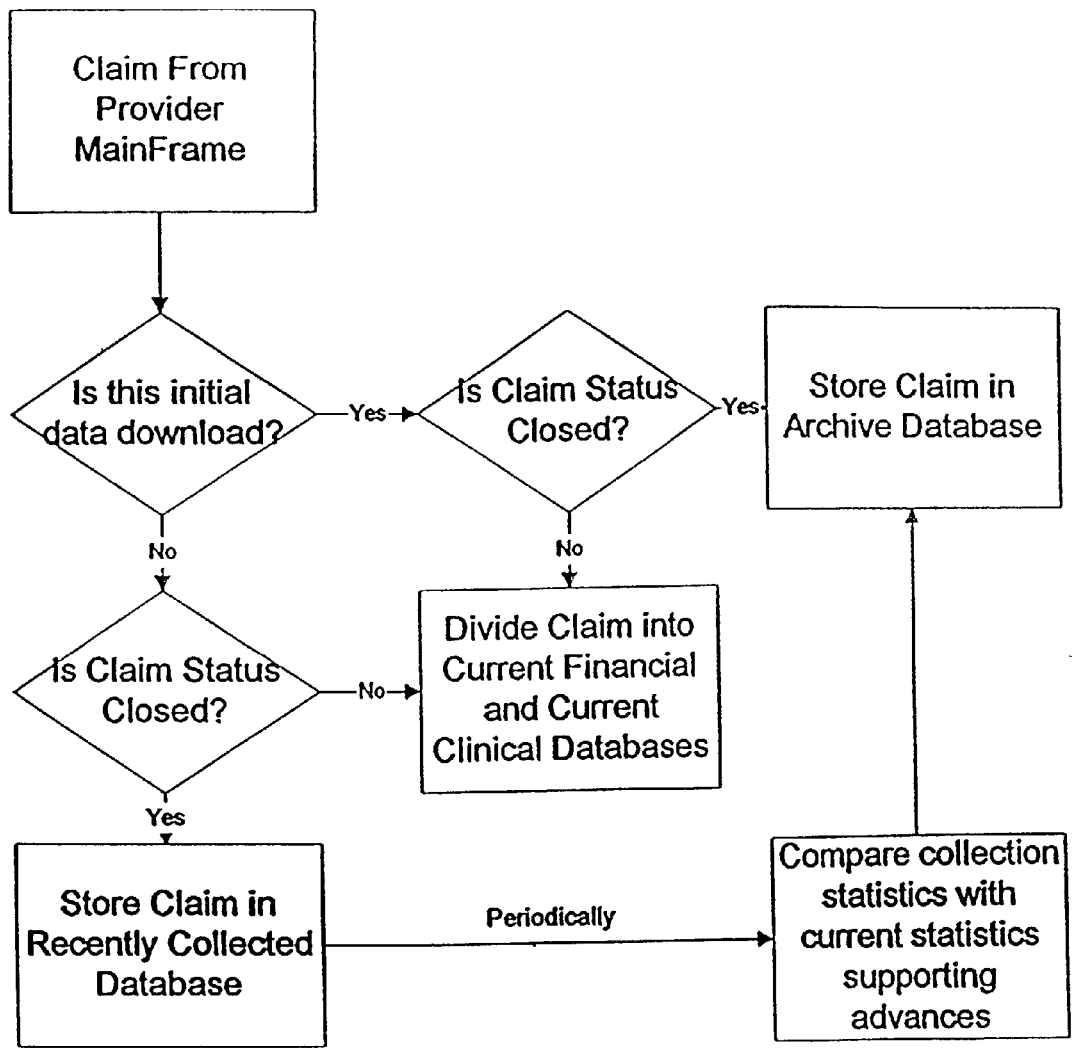
FIG. 15 illustrates the movement of claims through a provider's sentinel.

FIG. 15 shows how software 43 moves a claim between these four tables from the time it is originated to the time it is collected to the time it is statistically analyzed and permanently stored. When a providers claims are initially loaded on to the sentinel system 42, the sentinel 42 stores closed claim records in an archive table 45a (FIG. 7). If the claim status of the record is open, the financial and clinical portions are stored in a current financial record and a current clinical record, in tables 45c and 45d, respectively, maintained on sentinel 42's mass storage device. If it is not an initial download, that is the provider is actively selling claims to an SPE, and the claim status is open, the claim is processed into the current financial and current clinical tables. If the claim is closed, it is stored in the recently collected table 45b. Periodically, collection statistics on the claims in the recently collected table are generated for comparison with the collection statistics used to support the advance amounts. After this comparison, the claims are moved from the recently collected table 45b to the archive table 45a.

Figure 16:
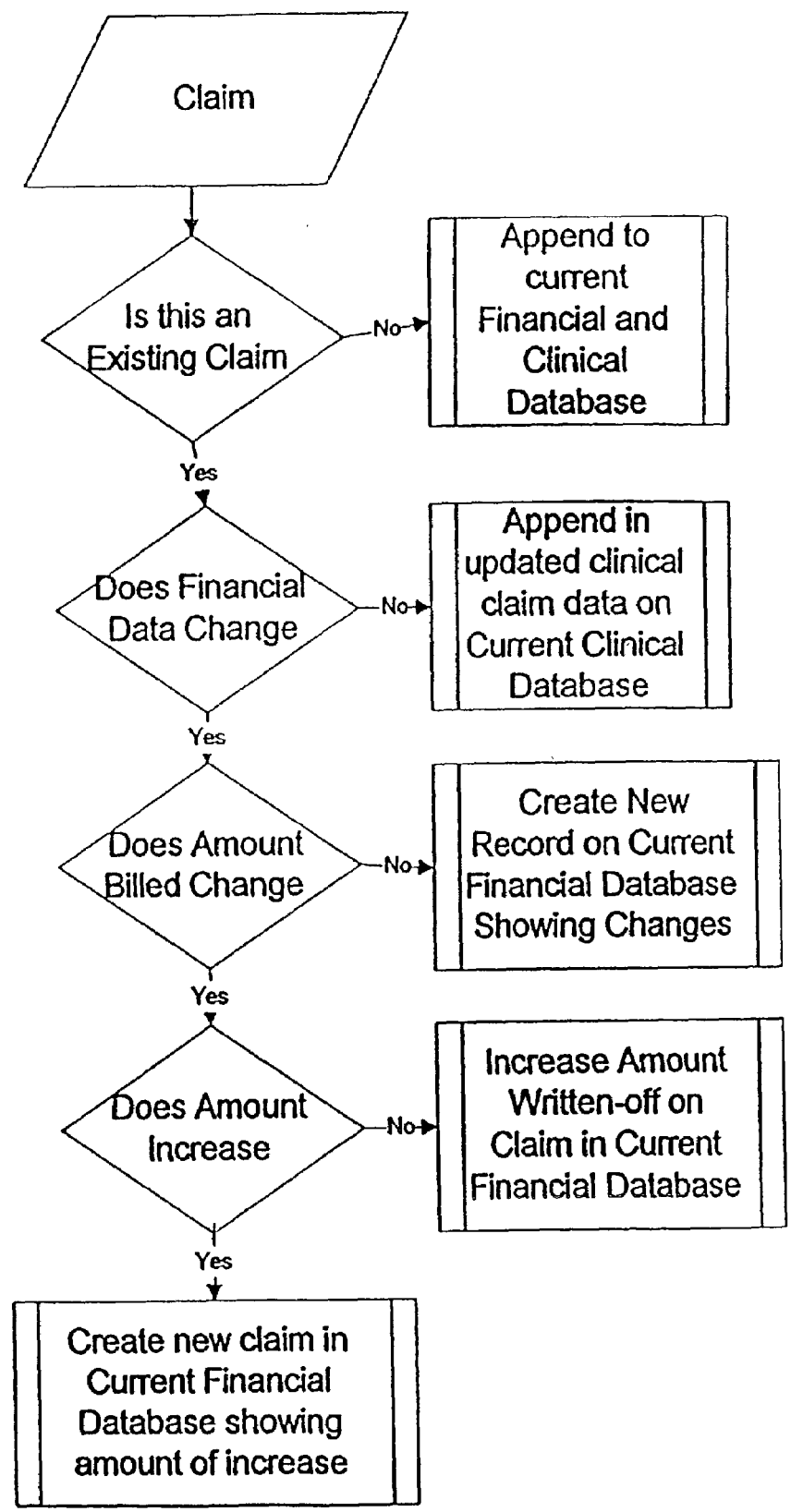
FIG. 16 illustrates the updating of claim data in a provider's sentinel.

FIG. 16 shows in more detail how the current financial and clinical claims database tables 45c and 45d, respectively are created and updated. Records in table 45c hold the financial data associated with medical claims. Records in table 45d hold the clinical data associated with medical claims. Thus, each claim has a financial record and a clinical record associated with it. FIG. 17 shows the data fields of the records in both the current financial and recently collected tables 45c and 45d respectively. The data for these fields is taken from the exported records (FIGS. 12A and 12B) from the provider's accounting system software 36. Each claim represented in a claim record has a claim status field. This field tells whether the record represents a new claim or an update to an existing claim. If it is a new claim, new corresponding financial and clinical records are created and appended to the end of the current financial and clinical tables 45c and 45d, respectively. If it is an update to an existing claim, the financial data portion of the claim is compared with the financial data portion of the existing claim as stored in the corresponding record of the current financial table 45c. If the financial portion does not change, then the updated clinical portion of the record is used to replace or overwrite the existing data in the record in the current clinical table 45d. If, upon comparison with the financial record, the amount billed doesn't change, then a new sub-record is created in the current financial table 45c reflecting the change in the financial portion of the claim. If the amount billed increases, then a new claim record is created in the current financial table 45c reflecting the amount of the increase. If the amount billed decreases, then the amount written-off is increased in the corresponding field of the corresponding record in the current financial table 45c.

Generation of Collection Statistics on Previously Collected Claims

The second step in setting up a provider to use the information management system 30 is to analyze the provider's claim history. This analysis produces two different types of statistics: net collectible value and a collection histogram.

As noted earlier, there are a variety of payment mechanisms used by the payers. Each of the different payment techniques has a different impact on predicting the net collectible value of a given claim. Payments based on diagnosis related groups (DRGs) tend to be a constant dollar amount for each DRG. This improves predictability by reducing the variation in payment amounts to virtually zero. Like DRG based payments, payments under a resource based value scale also tend to show little variation. This occurs because under this system of payments there are price caps on each of the services the provider performs. Payments made under either a percentage of provider's fees and charges or an estimate of usual and customary fees exhibit a much wider variation. Under both of these methods, both the payor and provider contribute to the variation. The payor through revision of the percentage or change in the estimate. The provider by changing billing practices. There are a variety of payment practices that can be grouped under the fee schedule heading. These include payment for specific services, negotiated bid, per diem or fixed reimbursement systems. Payments under fee schedules are highly predictable because they have been pre-arranged. Usually these payment vary by diagnosis related group. Another type of payment method is the use of a capitated payment. Under this payment mechanism, the provider receives a fixed fee (capitated payment) once a month. While this payment is highly predictable, its allocation across claims is arbitrary. For purposes of a commercial paper program, it is this once-a-month payment that must be secured against. All of these different payment methods make generating a statistical analysis more complicated. Regardless of payment method, it is essential that the period selected for generating claim statistics must have payments made under the same method as payments in the future are to be made.

Figure 18:
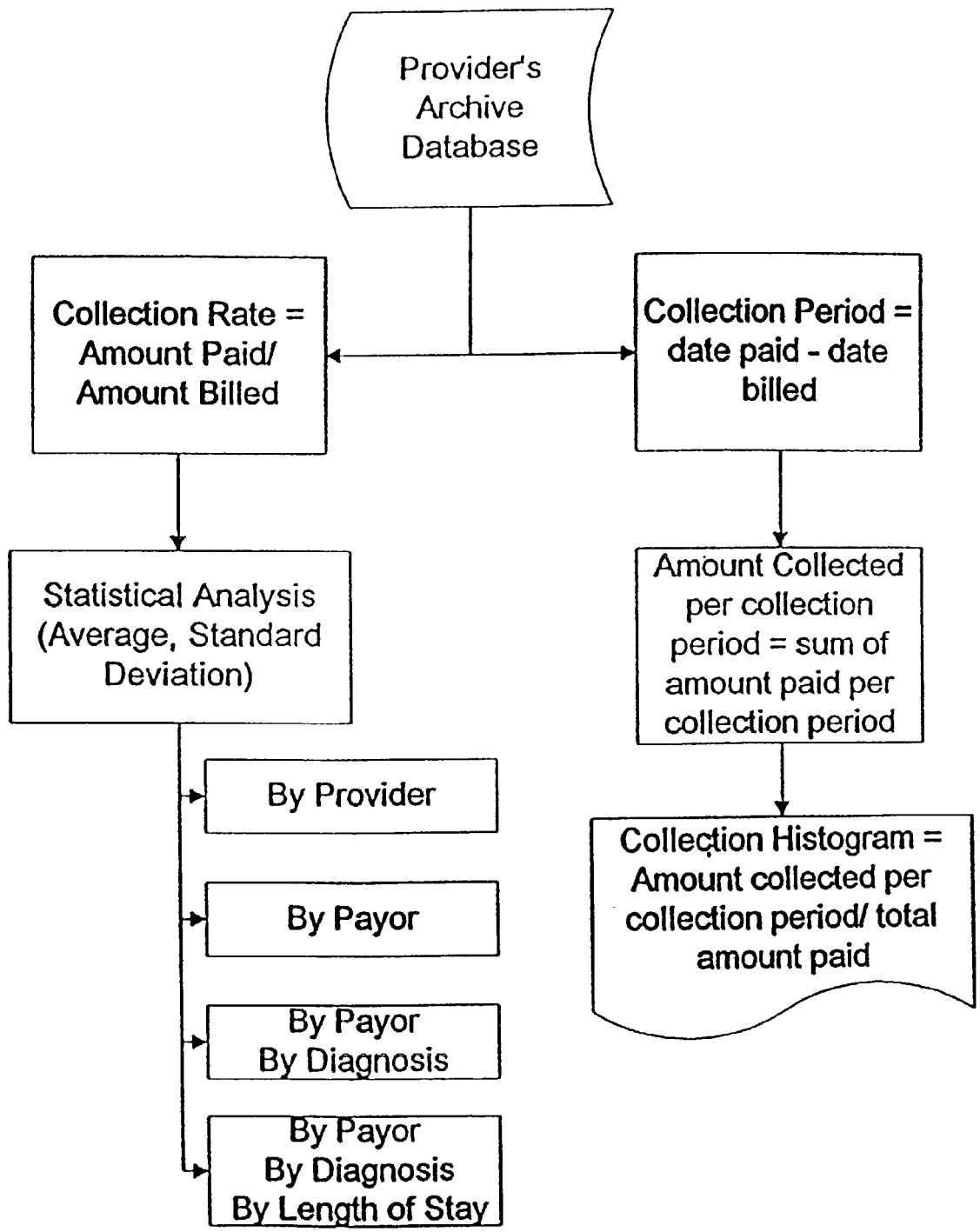
FIG. 18 illustrates the statistical analysis of historical claim data.

The statistical analysis of the historical claims data is preferably performed on eighteen to twenty-four months of historic collection data This analysis begins with the calculation of the collection rate on a claim by claim basis. The collection rate on an individual claim equals the amount paid on the claim divided by the amount billed on the claim Initially, net collectible value statistics are generated by examining the individual claim's collection rates on all claims in the archive table 45a. The individual collection rates are then summarized in statistics at four different level of inquiry: at the provider level; at the individual payor level; at the individual payor by diagnosis level; and at the individual payor by diagnosis by length of stay level. At each of these levels, an average, a standard deviation, a minimum value, a maximum value, a sum of the collection rates, a sum of the square of the collection rates and a count of the number of claims is calculated. They are saved in a table 45e called prior performance statistics. FIG. 18 shows how a provider's historic collection data is analyzed using software 43 executing on sentinel system 42.

The average net collectible value statistics are used to answer the question of if the provider has a claim against payor x of $y, how much will the provider get paid. The standard deviation shows how much the collection rate for individual claims varies from the average collection rate for all claims. The smaller the standard deviation, the higher the percentage of the average collection rate the commercial paper program can fund.

Figure 19:
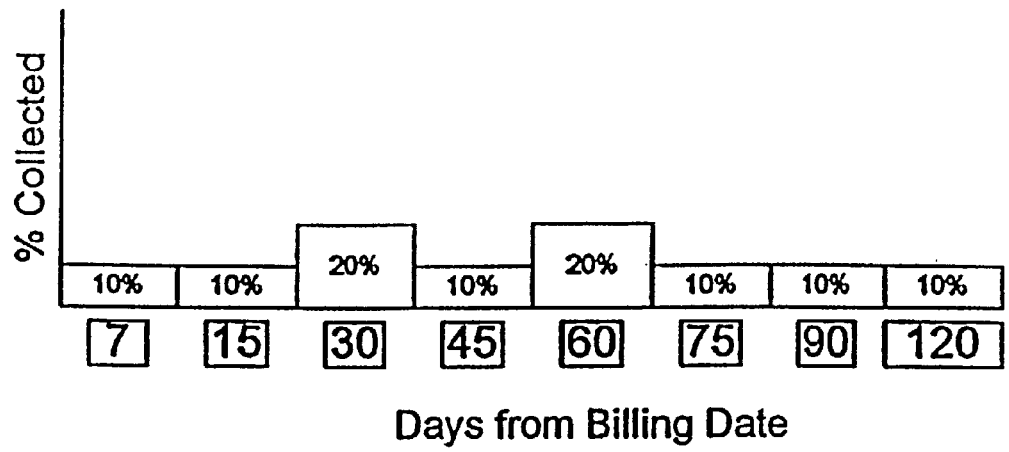
FIG. 19 illustrates a plot of a collection histogram.

A collection histogram answers the question of "When does the provider get paid?" The histogram is generated by first calculating the collection period for already paid claims. The collection period is the date the claim was paid minus the date the claim was billed. For each collection period, the amount paid is then summed. This result is then divided by the total dollar amount collected by the provider to create a histogram showing the percentage collected by days from billing. The collection histogram can also be calculated for individual payors. This is done by first calculating the collection period for already paid claims. For each collection period, the amount paid is then summed by payor. This result is then divided by the total dollar amount paid by each payor to create a series of histograms showing the percentage collected from a specific payor by days from billing. The statistics are stored in collection histogram table 45o on sentinel system 42. An example of a plotted collection histogram is shown in FIG. 19.

Software 43 uses the information calculated in both the collection rate analysis and the collection histogram creation is used to construct a payor effectiveness index. Within a given provider, an individual payor's effectiveness equals the average collection rate for the payor times the cumulative percentage of the payor's collection histogram for a specific time period divided by the average collection rate for the provider times the cumulative percentage of the provider's collection histogram for the same specific time. The index number is calculated by multiplying the individual payor's effectiveness by one hundred. The payor effectiveness data is saved in a payor effectiveness table 45n. The payor's effectiveness index is then reported to both the provider and the commercial paper program sponsor. The report to the provider also includes two size indices. The amount paid index is calculated by dividing the total amount paid by a payor by the total amount paid by all payors and then multiplying by one hundred. The amount billed index is calculated by dividing the total amount billed to the payor by the total amount billed to all payors and then multiplying by one hundred.

Formation and Updating of Daily Pools

Figure 20:
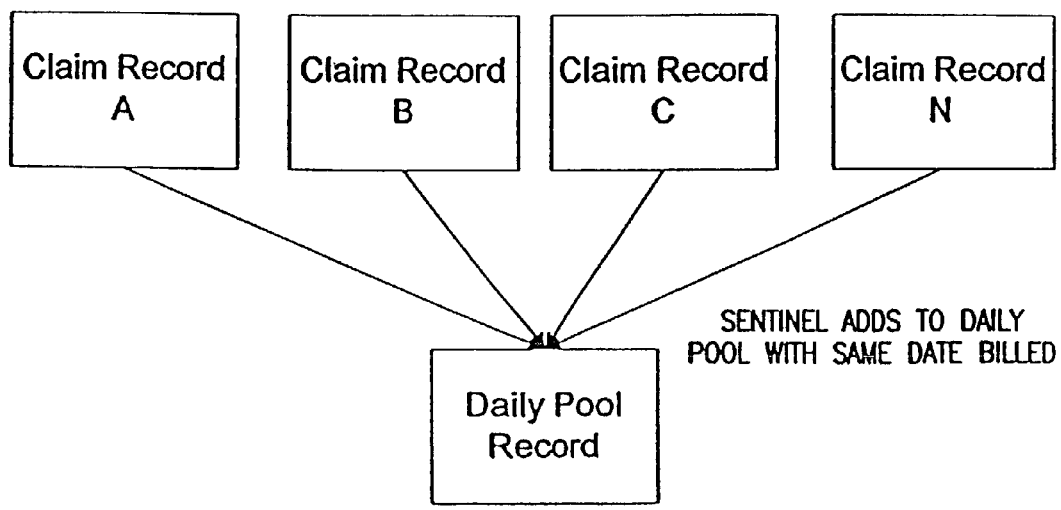
FIG. 20 illustrates the creation of a daily pool record from medical claims.
Figure 21:
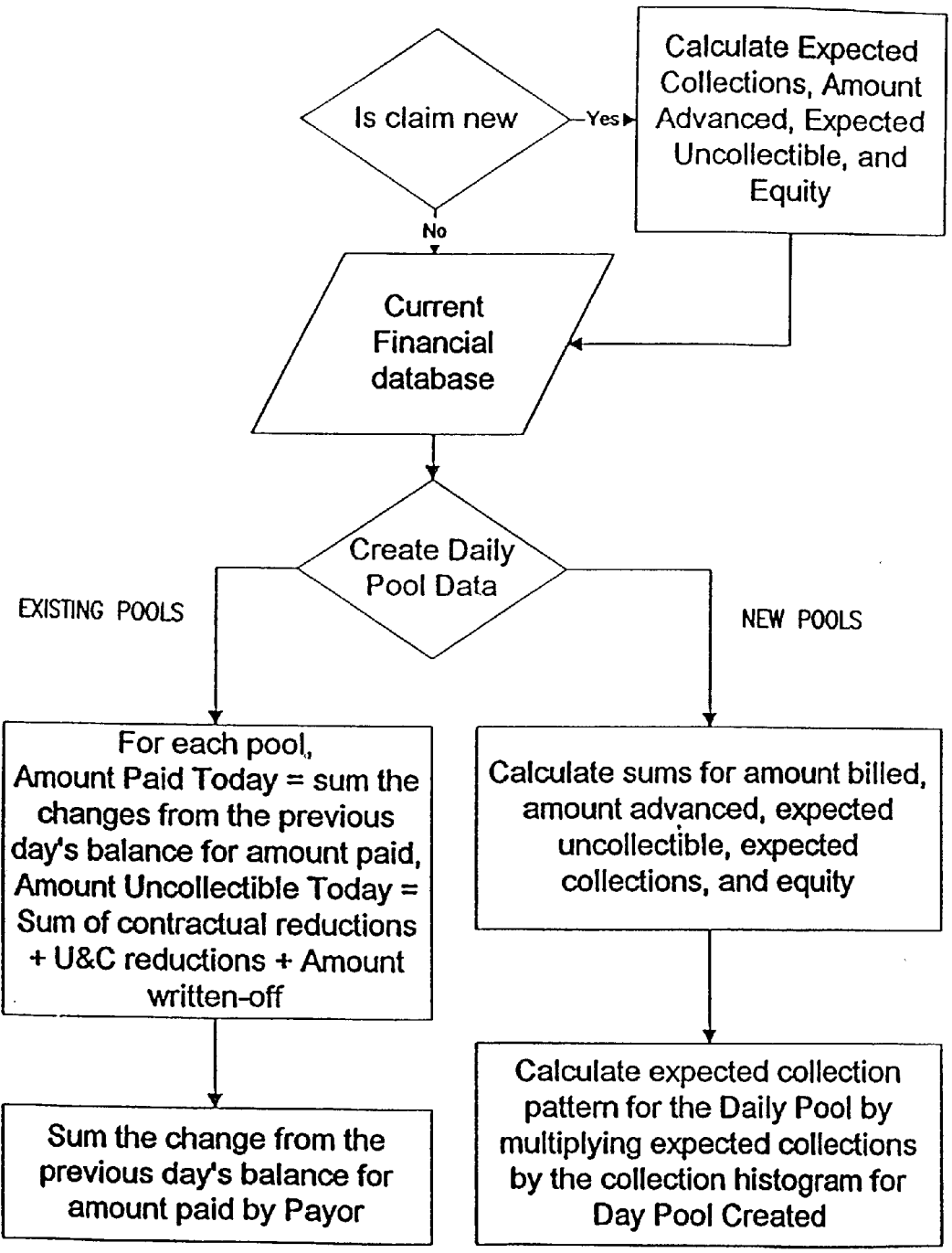
FIG. 21 illustrates the formation of a daily pool and updating.

The next step in bringing in a provider into the information management system 30 is the consolidation or updating of current outstanding claims and the capturing of new claims in trackable periodic units. For example, for large providers, the sentinel system 42 creates daily pools out of the providers claims data. FIG. 20 illustrates generally how claim records having the same date are used to form each daily pool record. As described above, new or updated claims have their financial data added to a current financial table 45c. FIG. 21 illustrates how software 43 forms this data into daily pools. All claims in a "daily pool" share the same date billed. Prior to forming the pool, the healthcare provider must select the commercial paper program that the pool is to go in to. The result of this choice determines which contract advance rates are to be used. Then, four additional data fields are calculated for each claim. These fields are shown in FIG. 22. As illustrated in FIG. 21, the current financial table 45c is reviewed, and if a claim is new, the software calculates the amount advanced, the expected collections, the expected uncollectible, and the equity. These new fields are added to the claim record, and the record is added to the current financial table 45c.

A daily pool record is created for each pool and stored in new daily pool table 45g maintained on sentinel system 42 and shown in more detail in FIG. 12A. For new pools, the sums for amount billed, amount advanced, expected uncollectible, expected collection, and equity are calculated from the claims in the pool, or obtained from claim records. Next, the expected collection pattern for the daily pool is determined by multiplying the total expected collections by the collection histogram for the pool. This data is stored in expected collection table 45k.

Software 43 of the sentinel system 42 tracks changes in existing daily pools. The software sums all of the changes that have occurred to the pool since the previous day. This involves calculating totals for the changes in the amount paid, contractual reductions, usual and customary reduction, and amount written-off fields from the previous day's balance. Realized uncollectible is calculated for each existing daily pool by adding contractual reductions, usual and customary reduction and amount written-off. The amount paid and the calculated realized uncollectible are saved in changes to existing daily pool table 45h.

The total amount paid by individual payor is calculated by summing the change in amount paid for all claims by individual payor. This data is stored in the daily payor collection table 45q.

Figure 24:
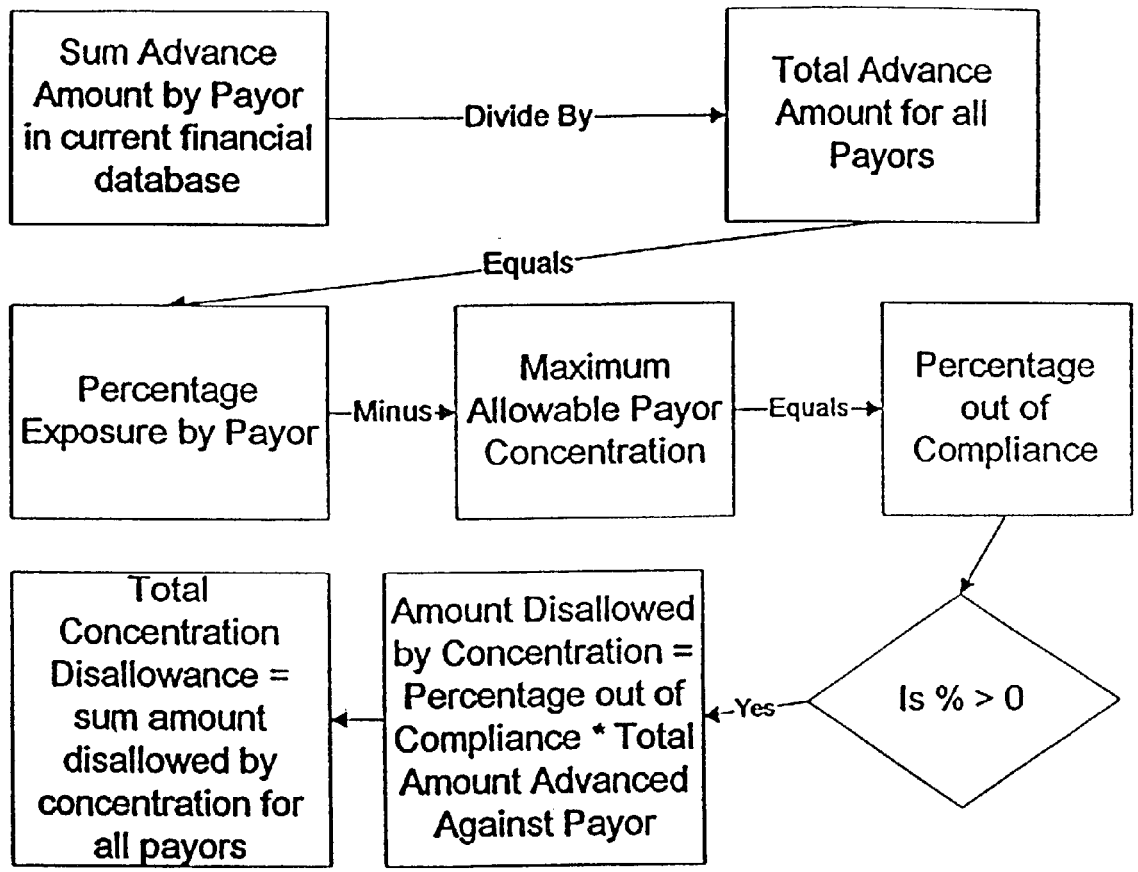
FIG. 24 illustrates the determination of payor concentration.

Commercial paper programs set restrictions on the exposure to any credit risk that the program will take on. This exposure is usually handled by limiting the percentage that any credit can be of the total credit extended. When each pool is formed, the credit exposure is recalculated. FIG. 24 illustrates how software 43 calculates the percentage concentration for any payor and how compliance with the commercial paper program's restrictions is enforced. The first step in calculating payor concentration is to calculate the total amount advanced to each specific payor in the current financial table 45c. This amount is then divided by the total amount advanced to all payors. The result is the percentage exposure to each payor. The commercial paper program's maximum guidelines is then subtracted from the percentage exposure. If the results of this subtraction are greater than zero, then this payor has exceeded its limit. Where the results of the subtraction are greater than zero, the difference is multiplied by the total amount advanced to determine the amount disallowed for over concentration. The total amount of disallowance is then summed. This disallowance is stored in compliance table 45j.

Performance Tracking

Figure 25:
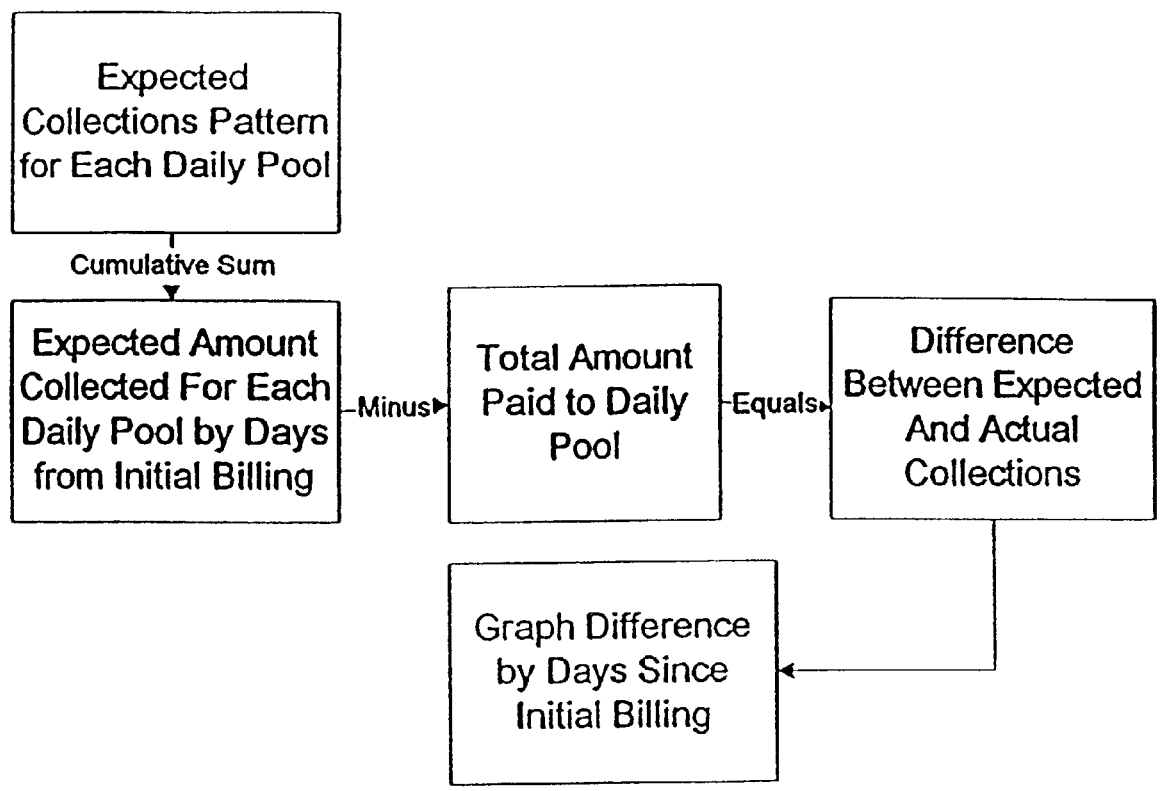
FIG. 25 illustrates a collection tracking flowchart for daily pools.
Figure 26:
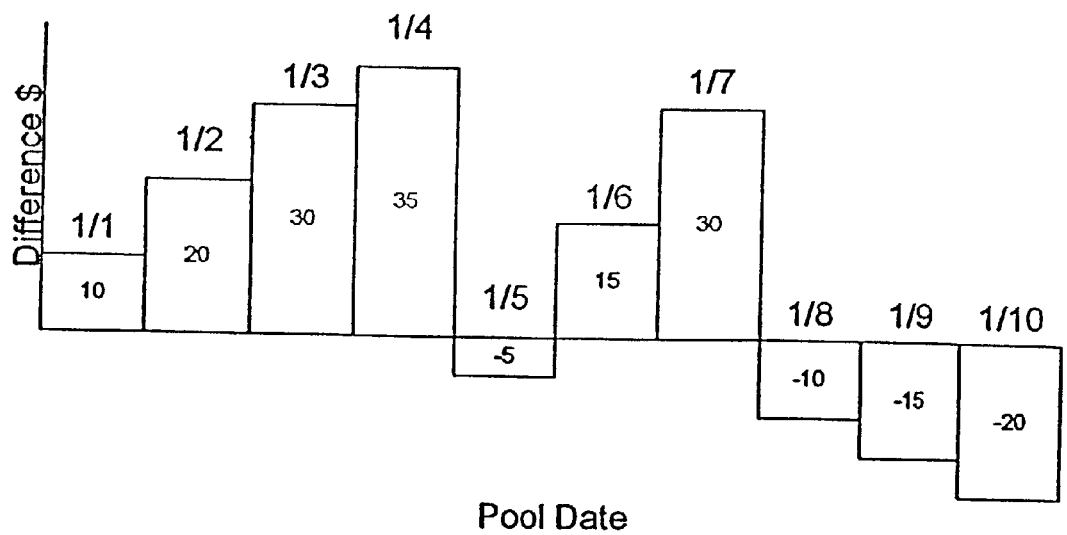
FIG. 26 illustrates a plot of actual vs. expected collections for a pool.

One of the major requirements of a commercial paper program is that the provider be able to track the performance of its receivables on an ongoing basis. FIG. 25 shows how software 43 tracks collections by pool. Collections are tracked by comparing actual collections for a daily pool (as determined from financial claim records) with expected collections for that pool. The starting point for this comparison is the expected collection pattern for the pool as previously determined (see FIGS. 18 and 19). The expected amount collected from day of billing is then calculated by running a cumulative sum on the expected collection pattern. The total amount paid on each daily pool is then subtracted from the expected amount collected for the appropriate day from billing. The results are saved in the collection performance tracking table 45l. The difference between expected and actual collections is also graphed and displayed or printed on sentinel system 42 by days since initial billing to be used by the provider. FIG. 26 illustrates this graphical display of actual vs. expected collections.

Calculating Current Performance Statistics

Another major requirement of a commercial paper program is that the provider engage in periodic tests to see whether the performance statistics on recently collected claims are statistically the same as the performance statistics used when the latest contractual advance rates were established. After the provider has begun participating in a commercial paper program, as current outstanding claims are paid off, these claims are stored in the recently collected table 45b. The collection rates in this table are periodically statistically analyzed by software 43. There are seven statistics calculated: an average, a standard deviation, a minimum value, a maximum value, a sum of all the collection rates, a sum of the square of the collection rates, and a count of the number of claims. The statistics are saved in the current performance statistic table 45e.

Payor performance can also be measured by how quickly the payor pays on the claims. A matrix can be calculated which shows all the payors for a given provider and their average days to payment. This matrix is calculated by finding the day from billing on the collection histograms for individual payors where it is estimated that fifty percent of the receivable will be collected. This day from billing is then shown for all payors. Another payment analysis would be to look at the days from billing by procedure. This would involve calculating collection histograms for individual payors by procedure and then finding the day where fifty percent of the receivables have been paid. This data is saved in collection time table 45r.

The line item information in a provider claim record can be used to create a revenue analysis by service by payor. This analysis involves determining how much each payor pays for a specific service. Each claim has the line item detail to show what amount was billed for a specific service and how much was paid by the payor. The revenue analysis would calculate an average payment for each service for each payor. These averages per payor could then be compared for a specific service. This type of data would be useful for subsequent negotiations with the payors. The results of these analyses are stored in revenue analysis table 45s.

Data Transfer between Sentinel and Central Processing System

The sentinel system 42 transmits data to the central location daily. FIGS. 23A and 23B show all of the data included in the master file 45m that are to be transmitted daily. The master file 45m is updated daily and stored on system 42 before being transmitted. As shown in FIGS. 23A and 23B, the new daily pool data includes a record for the new pool formed on the day of transmission, including the date billed, amount billed, amount advanced, expected uncollectible, expected collections, and equity. The expected collection histogram data contains a histogram showing the expected collection pattern for the pool. The changes to existing daily pool data contains for each existing pool a record which specifies the date billed, the amount paid today, and the realized uncollectible. The prior performance statistics data and the current performance statistics data contain the data for, respectively, both the archive table and the recently collected table. This data includes the average collection rate, standard deviation, sum of all collection rates, sum of all collection rates squared, and the count of number of claims in the analysis. The compliance data includes the total concentration disallowance. The collection performance tracking data contains the graphical information which shows the difference between expected and actual collections by day from billing. The daily payor collection data includes data on the amount billed by payor and the amount paid by payor. Finally, the payor effectiveness data contains the payor effectiveness index.

The sentinel 42 receives summary data back from the central location 50. This data includes periodic updates to both the advance rates for the various conduits that the provider has contracts with as well as conduit specified payor limits. The daily data received includes financial statements (balance sheet, income statement, and cash flow statement) and a collection reconciliation report showing differences between what the provider reported as amount paid and what the conduit reported as amount paid. Using software 43, provider personnel can access these reports as well as a collection tracking report by payor at any time during the day.

Sentinel at SPE's Operating Agent Location

Figure 27:
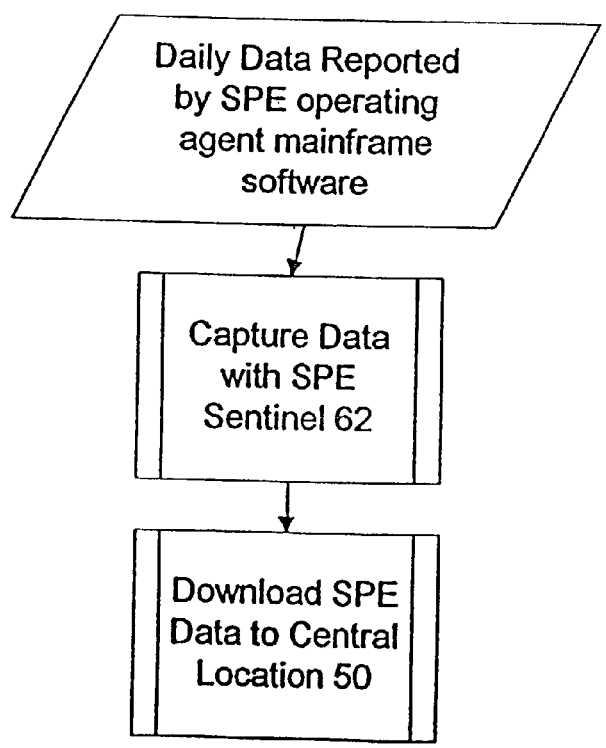
FIG. 27 illustrates the downloading of data from a SPE computer system to the computer system at the central location.

The sentinel system 62 at the SPE's operating agent location 60 has two primary functions: capture commercial paper program data generated by the operating agent for transmission to the central location 50 and providing access to the operating agent for several reports generated at the central location. The commercial paper program's data is also downloaded into a local sentinel 62 from the operating agent's computing system 66 before being transmitted to the central location 50. FIG. 27 shows how software 63 takes each day's records from the SPE and records them in a SPE table maintained on the sentinel system 62 for transmission to the central location 50. FIG. 28 shows the data fields captured from the SPE's mainframe 66. This data can be downloaded as illustrated in FIG. 13 in a variety of file languages including, either ASCII or DBF.

Unlike the provider, the data from the SPE is already in summary form. The reason that the SPE reports summary data is a function of how the data is obtained or generated by the SPE. For example, daily collection data is obtained by looking at cash receipts from individual payors made on the provider's behalf in the SPE's bank account. For another example, individual provider interest expense is calculated by determining the daily interest expense for the SPE and then charging the provider for the amount of this interest expense which corresponds to the percentage of the amount advanced to the provider divided by total advances from the SPE. One of the primary functions of the information management system 30 is to reconcile the summary level data from the SPE with the detail level data at the individual provider level.

File Server at Central Location

As described generally above with respect to FIG. 9, software 53 executing on the computer system 51 at the central location 50 has several functions: it receives the data from the provider and SPE sentinels 42 and 62 (53a and 53b); it captures the data from the SPE's commercial paper dealer (53c) and the contract between SPE and provider (53d); it reconciles all of the detail and summary level data (53e); it reports a credit scoring index based on each provider's payor effectiveness index and the credit rating for the payor (53l); it generates the financial accounting statements (53g) for the individual providers by tracking daily pools (53g); it creates asset/liability management reports to monitor and control interest rate and liquidity risk (53m); it reports financial statements (53f) to individual providers and concentration and tracking statistics (53i) to SPE's; it calculates performance statistics (53j), and it includes a contact management system (53k). As also noted above, FIG. 10 illustrates various tables and files 55 maintained on the file serve 56 at the central location 50, to be described below.

The contact management system executing on the central location computer system 51 keeps track of all of the parties who act as a source of information to the management information system 30. The contact system uses the data fields as shown in FIG. 29 for each SPE, provider, and commercial paper dealer. As illustrated in FIG. 10, four separate files 55a, 55b, 55c and 55d are set up to keep a record of the SPE/conduit, providers, commercial paper dealers, and payors respectively.

Figure 30:
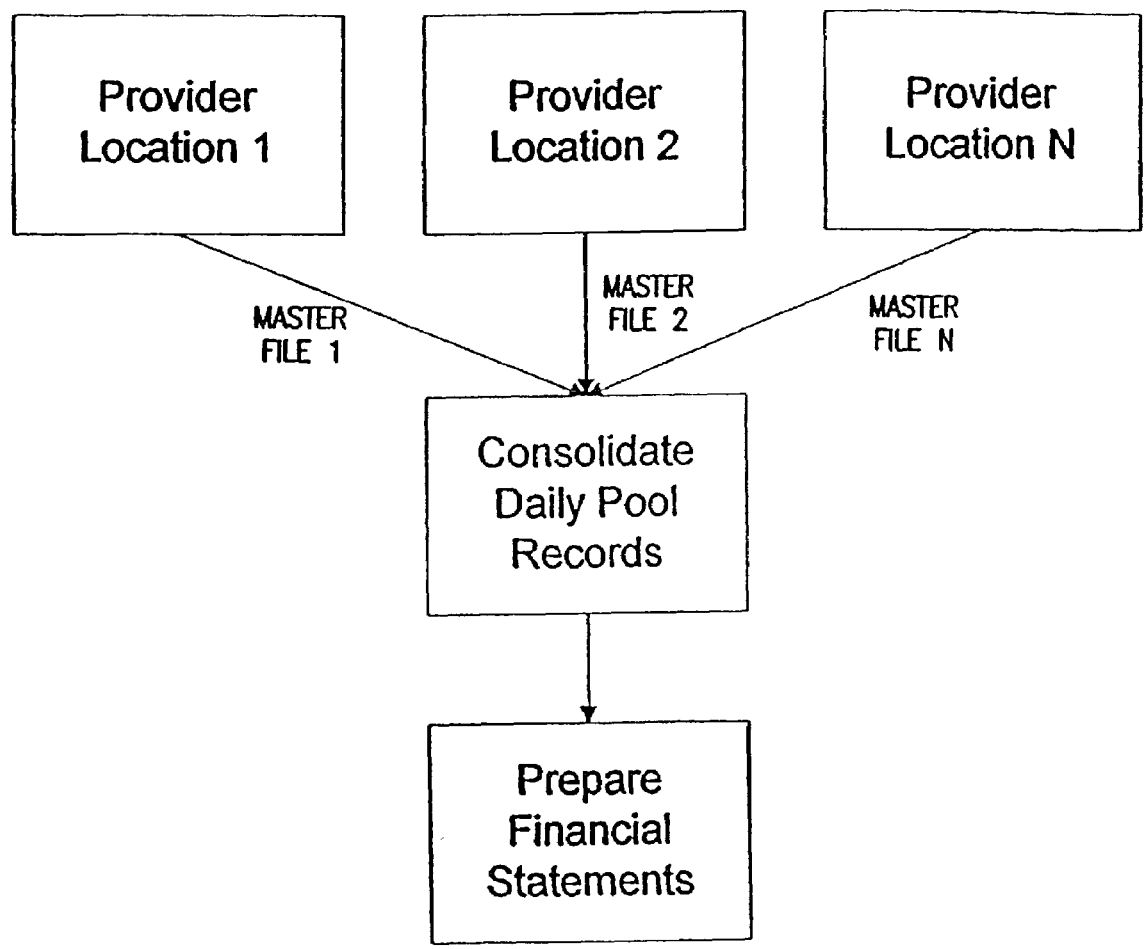
FIG. 30 illustrates the consolidation of data from several different provider locations into a consolidated daily pool at the central location.

As noted above, the file server 56 receives information from both the provider and the SPE's locations. This data is electronically transmitted from the sentinels 42 and 62 at each location. The data is received by I/O computer 52 which scans it for viruses. If no viruses are detected, this information is then passed over the network 54 to the file server 56. The data is sent in electronic preassigned tables in an "mdb" file (Microsoft Database) with a specific provider designation on the file. The file server attaches the data in each of the preassigned tables for use in additional analyses. The preassigned tables are shown in FIG. 10. If a single provider is transmitting files to the central location 50 from multiple locations 40, the data in the files 43m is consolidated by central location software before further processing, as generally illustrated in FIG. 30. This consolidation is accomplished by software 53 by tracking each location separately and combining all of a provider's data together as it is needed for different calculations and reports. For example, to reconcile the amount the SPE says it advanced to the provider with the amount the provider's detail data shows should have been advanced, all of the advance amounts reported in the new daily pool table from the different locations need to be added together.

There are three types of data that is manually entered into the file server at the central location: payor credit rating related, contract related and commercial paper related. The file server tracks the credit rating on each individual payor's claim paying ability. The payor credit table (55t) contains the data fields shown in FIG. 31.

Figure 32:
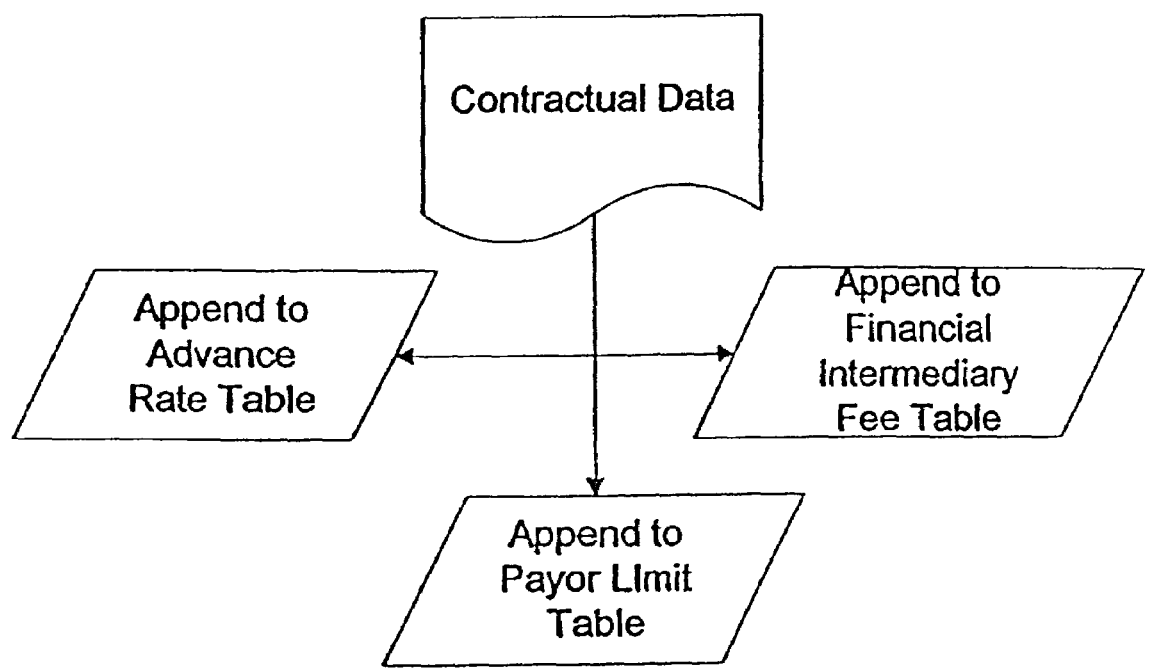
FIG. 32 illustrates the inputting of contractual data at the central location computer system.

As illustrated in FIG. 32, software 53 tracks the information embodied in the contract between the commercial paper program and the provider. In the contract, the rate at which the SPE is to advance money against receivables of specific payors is documented. This is kept track of in a table 55o called advance rates, which also includes a provider and payor ID field. The contract also documents the fees that the various financial intermediaries involved in the SPE can charge. Financial intermediaries may include banks, monoline insurers, commercial paper dealers, operating agents and SPE sponsors. This information is tracked in a table 55p called third party fees. It also includes a provider and SPE ID field. Lastly, the contract specifies the maximum percentage an individual payor can represent of the claims sold to the SPE by a provider. These percentages are maintained in a table 55q called payor limit. The payor limit table 55q also includes SPE and provider ID fields.

Figure 34:
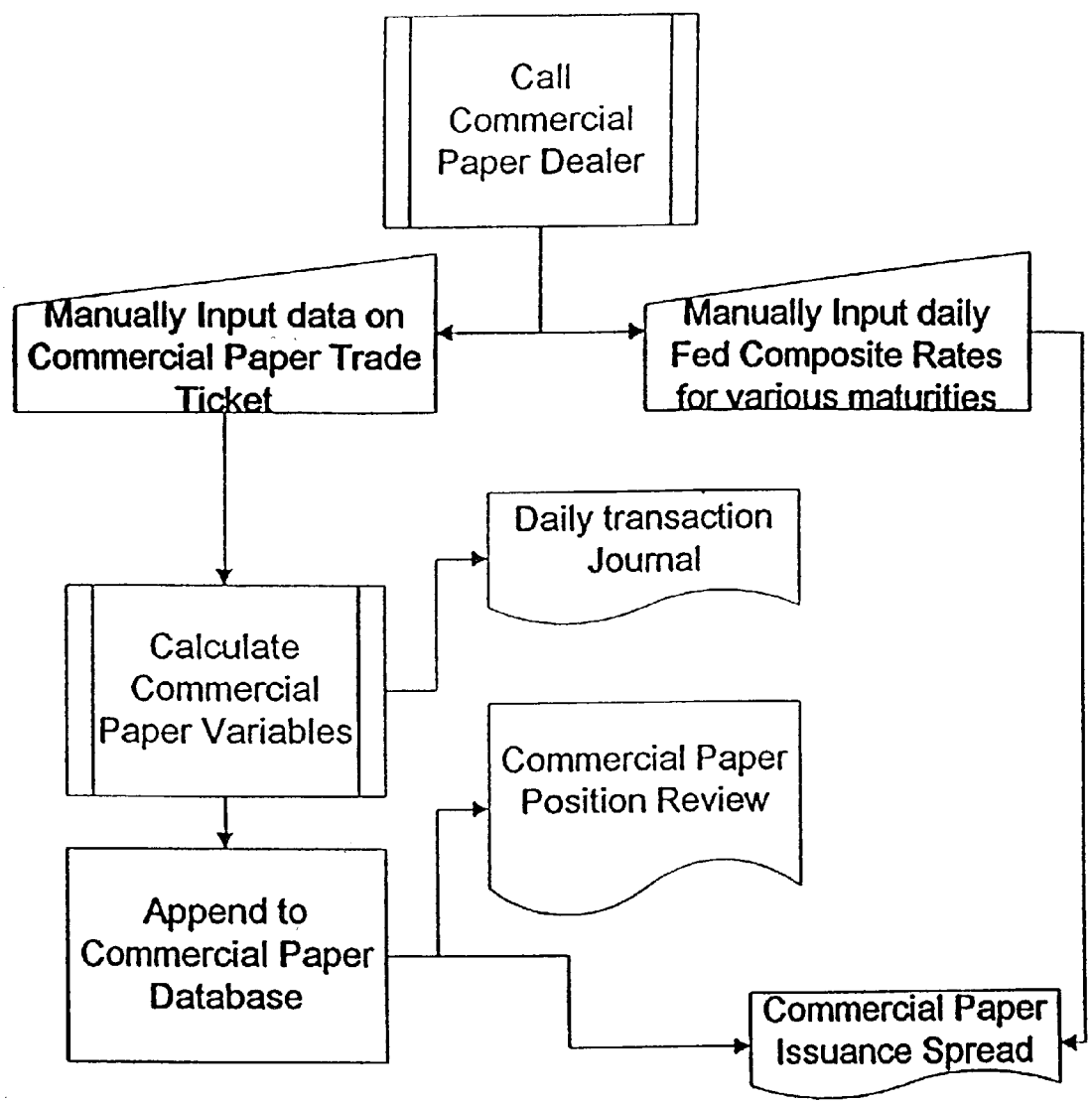
FIG. 34 illustrates the input procedure for commercial paper data.

The last source of data is the commercial paper dealer. This data is captured in the form of a trade ticket which is entered into a computer at the central location. As the trade ticket is entered into the computer, several additional data fields are calculated. FIG. 33 shows the initially entered fields and the calculated fields. FIG. 34 shows how the commercial paper information is entered using software 53 and stored in table 55e and 55u. The commercial paper dealer is called. The commercial paper trade tickets, the source of the information for table 55e, and daily federal composite rates for various maturities, the source of the information for table 55u, are input. Commercial paper variables are calculated and entered in the commercial paper table 55e. The records for each trade are entered into the daily transaction journal in the commercial paper database table 55e. The commercial paper position review and commercial paper issuance spread are recorded and reported.

Figure 35:
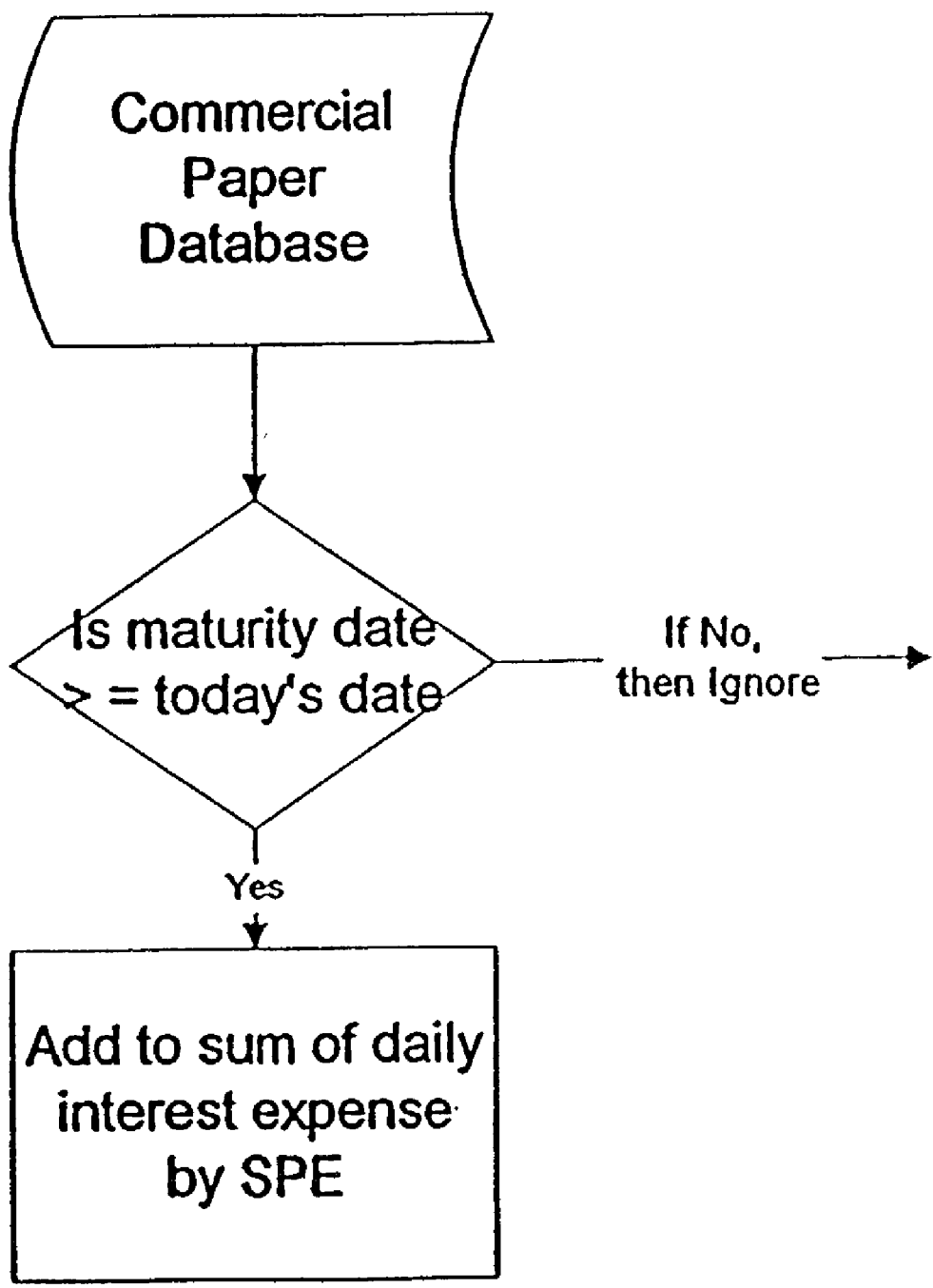
FIG. 35 illustrates the determination of daily interest expense by SPE from commercial paper.

After having collected the data from the commercial paper dealer and the contract, software 53 performs any calculation necessary to generate the information needed to run a data reconciliation analysis. The data from the commercial paper table 55e is used to create daily interest expense for each SPE or conduit, as shown in FIG. 35. This is done by summing by SPE the daily interest expense for each piece of commercial paper that has not yet matured in the conduit. If the maturity date for a commercial paper instrument is greater than or equal to the day's date, the daily interest expense by SPE is added to the sum of daily interest expense. The results are saved in the detail based daily interest expense table 55v.

Figure 36:
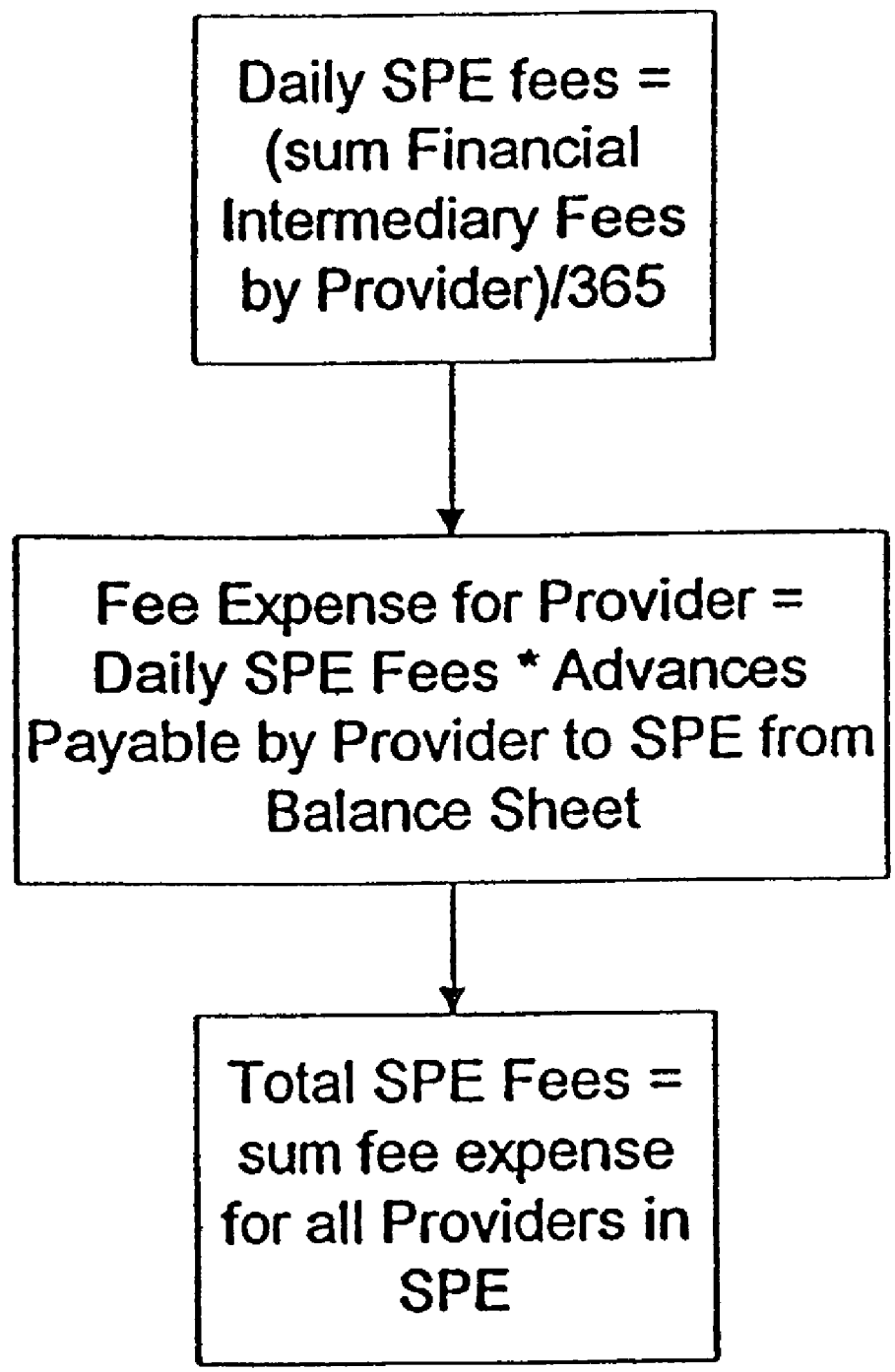
FIG. 36 illustrates the total fee expense calculation.

FIG. 36 illustrates the total fee expense calculation performed by software 53. Daily SPE fees by provider by SPE are determined by summing the financial intermediary fees (from third party fees table 55p) by provider by SPE and dividing by 365. SPE Fee expenses equal the daily SPE fee by provider by SPE times the total advances payable to the SPE from the provider in the balance sheet. The total SPE fees by conduit are equal to the sum of each provider's SPE fee expenses for that conduit. The results are saved in the detail based third party fee file 55w.

Figure 37:
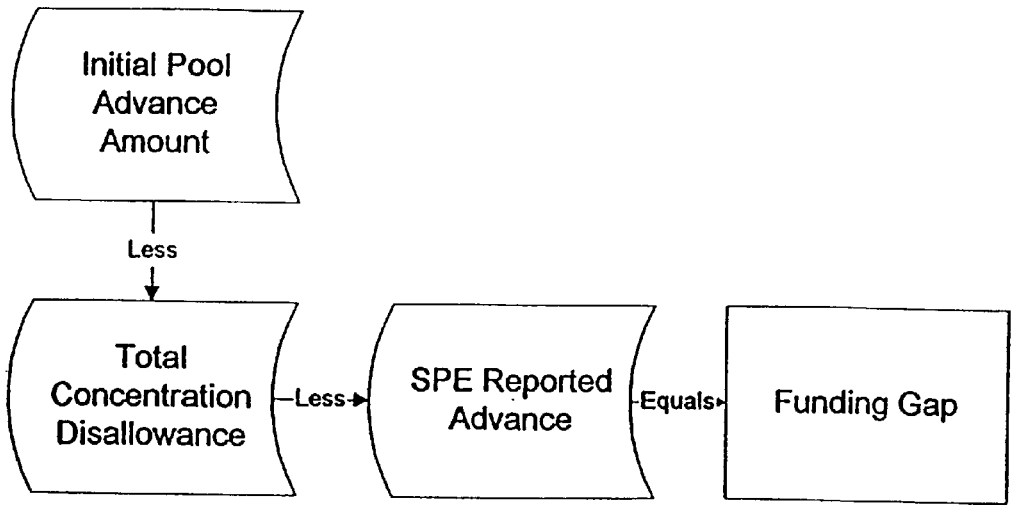
FIGS. 37, 38, 39 and 40 illustrate advance, collection, interest expense and third party fee reconciliation, respectively.

At this point, all of the data that is needed for running reconciliations between various data sources is now available. Reconciliations are performed using software 53. There are four basic types of reconciliations. First, the amount the SPE's report they advanced, stored in SPE table 55j is compared with the amount that the provider claim detail shows they should have advanced as stored in downloaded daily pool records. As shown in FIG. 37, the funding gap equals the advance amount from the new daily pool record sent over by the provider sentinel 42 minus the total concentration disallowance from the payor concentration data sent over by the provider sentinel system 42 minus the reported advance from the daily advance data sent over by the SPE sentinel 62. The funding gap calculation is saved in a reconciliation table 55r.

Figure 38:
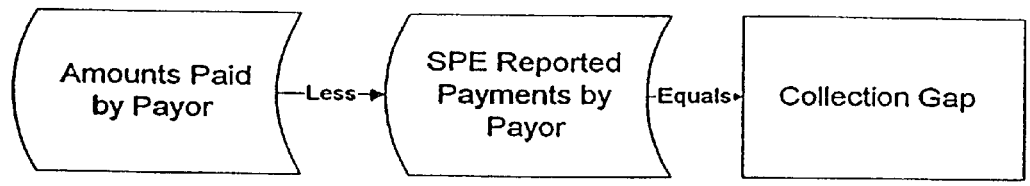

Second, as shown in FIG. 38, the amount the SPE's report they collected as specified in SPE table 55j is compared with the amount that the provider claim detail shows they should have collected. The collection gap equals the amount paid by payor in the daily payor collection data sent over in the master file 45m (and stored in file 55h on the system 51) by the provider sentinel system 42 minus the amount received from payor in the payments received data (FIG. 28) sent over by the SPE sentinel system 62. The collection gap is saved in the reconciliation table 55r.

Figure 39:
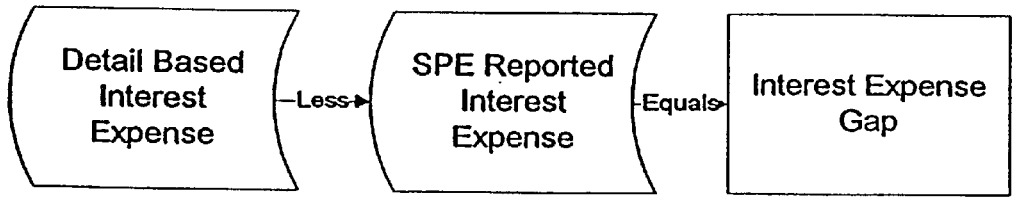

Third, as shown in FIG. 39, the amount the SPE's report for daily interest expense is compared with the amount of daily interest expense calculated from the commercial paper table 55e. The interest expense gap equals the interest expense calculated from the commercial paper table 55e minus interest expense as reported in the interest expense records (FIG. 28) sent over by the SPE sentinel 62. The interest expense gap is saved in the reconciliation table 55r.

Figure 40:
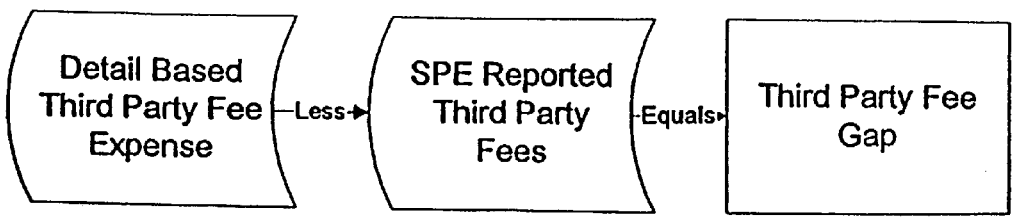

Fourth as shown in FIG. 40, the amount the SPE's report for daily financial intermediary (third party) fee expense is compared with the amount of daily fee expense calculated from the fee table 55p and the daily pool balance sheets 55k.

The third party fee gap equals the difference in these fees. The third party fee gap is saved in the reconciliation table 55r.

Software 53 does not make any adjustments for gaps uncovered when the reconciliation analysis is performed. No adjustments are made because each of these gaps should be eliminated by the responsible party within a twenty-four hour period. For example, an underadvance by the SPE yesterday can be cured by advancing more today. Using I/O computer 52, software 53 transmits the results of the reconciliation analysis stored in table 55r to the provider sentinel 42 and the SPE sentinel 62 so that they can be reviewed.

The preparation of the financial accounting statements and reports involves tracking twelve data fields for each pool. FIG. 41 shows these fields. The financial statements for each pool are prepared daily in accordance with generally accepted accounting principals. The income statement is prepared reflecting accrual accounting.

The financial accounting for each pool begins with the appending of data from the new daily pool data (FIGS. 12A and 12B) sent over by the provider sentinel 42 to the balance sheet data 55k stored on the file server 56. After the pool has been in the balance sheet data 55k for one day, interest expense and fee expense are calculated on the amount in advance payable and retained earnings and the balance sheet data 55k is updated. Software 53 then looks into the changes in existing pools data sent over by the provider sentinel 42 in master file 43m to see if there have been any collections or realized uncollectibles. If there have been, then the accounts receivable and bad debt accounts are updated in the balance sheet data 55k. If there have been collections, then the amount of interest, fees and advances paid is calculated. The interest, fees and advance payable are then updated on the balance sheet data 55k. The process of calculating expenses, cash flow and updated balance sheets is repeated every day for the pool until the pool is closed.

Figure 42:
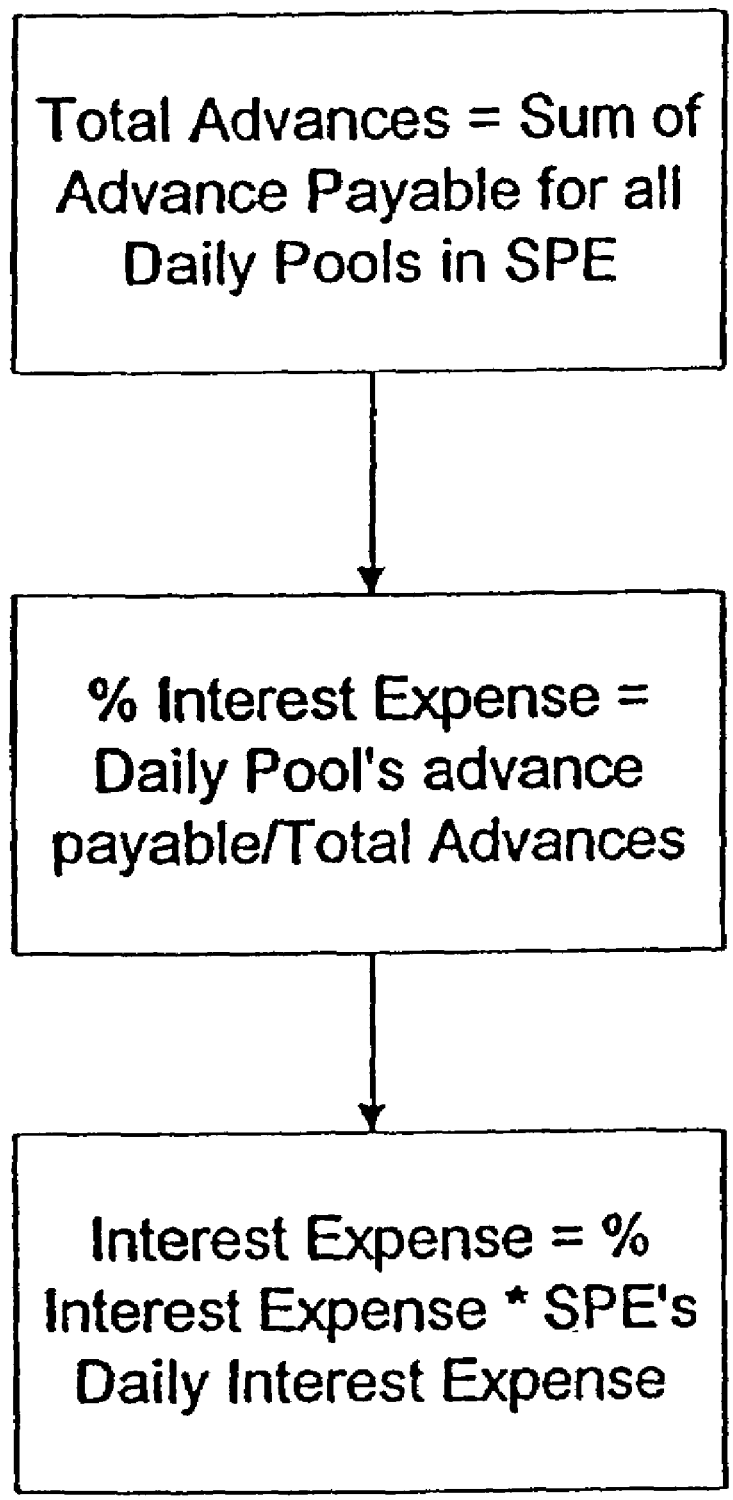
FIG. 42 illustrates allocation of SPE daily interest expense.
Figure 43:
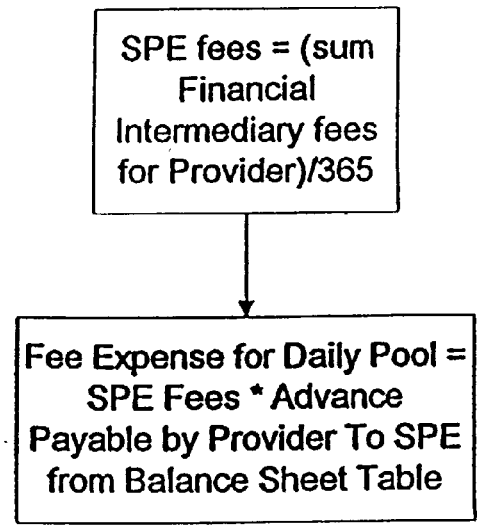
FIG. 43 illustrates daily pool fee expense calculation.

FIGS. 42 and 36 show how interest expense and fee expense are calculated for each pool by software 53. Interest expense is calculated for each daily pool by first calculating the total of the advance payable in the balance sheet data 55k for all the pools in a SPE. Each pool's advance payable is then divided by the total advance payable in the SPE to calculate that pool's percentage share of the interest expense. The pool's daily interest expense is then calculated by multiplying the pool's percentage share of the SPE's daily interest expense by the SPE's daily interest expense. The results are stored in the income statement data 55l.

For all pools, the daily financial intermediary (third party) fee expense equals the advance payable from the balance sheet data 55k times the total of the financial intermediary fees in the contract file 182 divided by 365. SPE fees for provider equal the sum of all financial intermediary fees for provider divided by 365. The SPE fee expense equals the sum of the SPE fees for provider times the total advance payable to provider from the balance sheet. The results are stored in the income statement data 55l.

Figure 44:
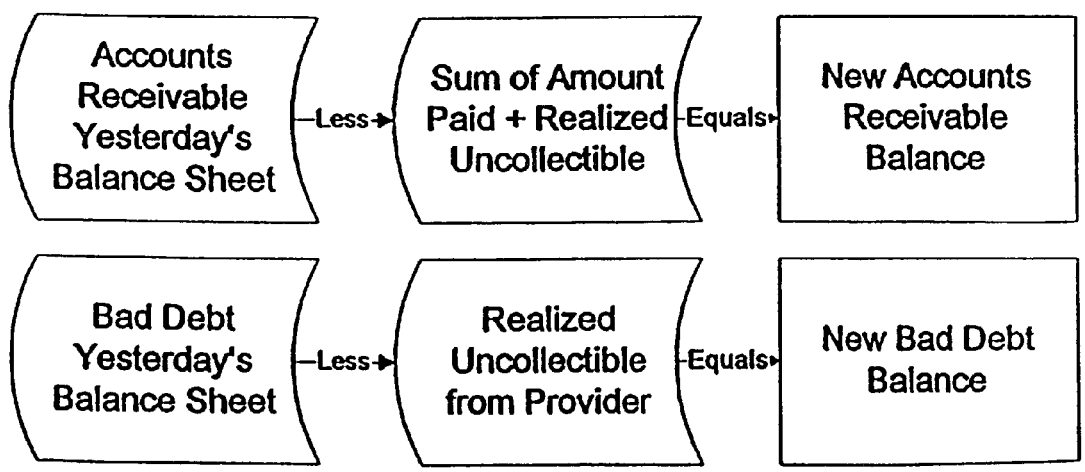
FIG. 44 illustrates the net receivable update.
Figure 45:
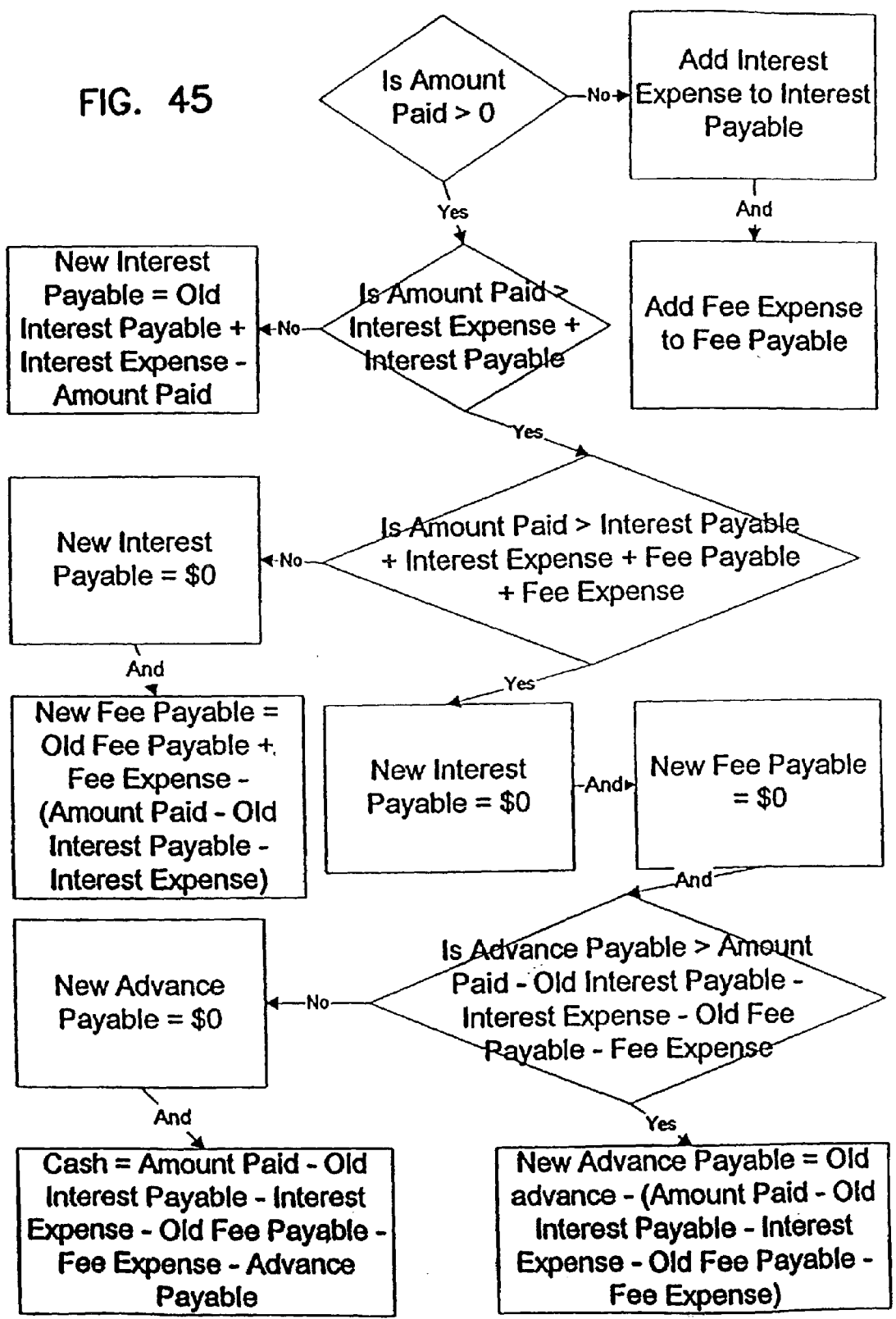
FIG. 45 illustrates the payables update.

FIG. 44 shows how accounts receivable and bad debt are updated daily for each pool. The opening accounts receivable balance for each daily pool is set equal to the amount billed by the provider for the pool date. The balance is reduced each day by the amount paid and the amount of the realized uncollectible for the pool. The opening bad debt balance for each daily pool is set equal to the expected uncollectible amount for the pool. The balance is reduced each day by the amount of the realized uncollectible for the pool. The results are stored in the balance sheet data 55k FIG. 45 shows how the accounts payable, namely advance payable, interest payable and fees payable, are updated for each daily pool balance sheet by software 53. For each daily pool, the initial balance in the advance payable account is set equal to the amount advanced. For each day that the pool has a balance greater than zero in its advance payable account, an interest expense and a fee expense are calculated. On those days that the pool does not have any collections, the interest expense is added to interest payable on the balance sheet to create the new interest payable amount and interest paid on the cash flow statement is set equal to zero. Also, the fee expense is added to fees payable on the balance sheet to create the new fees payable amount and the fee paid on the cash flow statement is set equal to zero. If the pool has any collections, the collections are used to pay down accounts in the following order: interest, fees, and then advances. If the amount collected is less than today's interest expense plus the interest payable on the balance sheet, then the total amount collected is applied to interest and the new interest payable amount becomes the difference between today's interest expense plus the interest payable on the balance sheet and the amount collected. Interest paid on the cash flow statement equals the amount collected and fee paid is set equal to zero. If the amount collected is greater than or equal to that day's interest expense plus the balance in the interest payable account, then an amount equal to the interest expense plus the interest payable is used to pay off these accounts. Interest paid on the cash flow statement equals the day's interest expense plus the balance in the interest payable account. If the excess is less than today's fee expense plus the balance in the fee payable account, then the new fee payable amount equals today's fee expense plus the balance in the fee payable account minus the excess. Fee paid in the cash flow statement equals the excess. If the excess is greater than or equal to today's fee expense plus the balance in the fee payable account, then an amount equal to today's fee expense plus the balance in the fee payable account is used to pay off these accounts. Fee paid in the cash flow statement equals today's fee expense plus the balance in the fee payable account. If there is any remaining cash, the cash is used to pay down the advance payable account to the point where either all of the cash has been used or all of the advance payable has been paid off. The advance paid in the cash flow statement equals the reduction in the advance payable.

Figure 46:
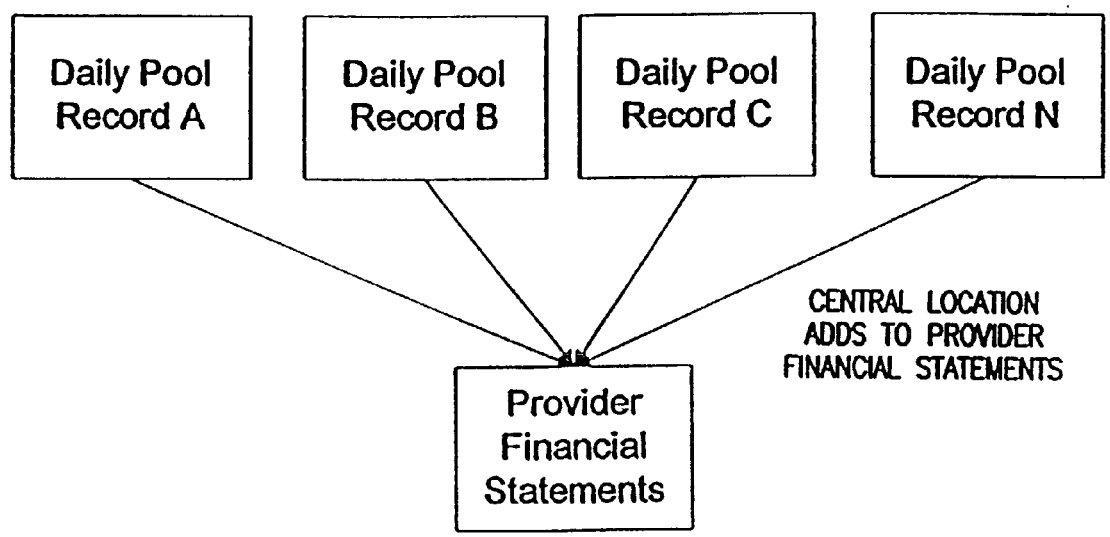
FIG. 46 illustrates the creation of a financial accounting report from a plurality of daily pool records.

After the accounting entries for each daily pool have been created, they are used in a conventional accounting package to create financial statements for both the daily pools and the providers, as generally illustrated in FIG. 46. The financial statements are recorded in a file and transmitted back to the sentinel 42 where they are reported daily to the provider and form the basis for the provider being able to audit its participation in a commercial paper program. Included with the financial statements is a settlement analysis. This analysis looks at how much cash should be paid to the provider each day. Cash paid to provider equals cash collected the previous day less interest paid less fees paid less advances paid plus new advances.

Comparing Current and Past Collection Statistics

In the contract between the SPE and the provider, there is a definition of how much change in the net collectible value statistics (average and standard deviation) triggers a change in the advance rates. The software 53 at the central location automatically reviews changes in the net collectible value statistics. There are three types of changes: changes which indicate that there should be a downward revision to the advance rates; changes which indicate that there should be an upward revision to the advance rates; and changes which indicate that the advance rate level is still appropriate. The performance statistics from the providers are analyzed for these three types of changes in an Excel spreadsheet. Unless a higher threshold is set by the SPE, the spreadsheet looks to capture changes by comparing the average net collectible value on recently collected claims with the range formed by adding or subtracting one standard deviation from the average net collectible value at the time the advance rates were set. Initially, the average net collectible value at the time the advance rates are set will be in the prior performance statistics table sent over by the sentinel. Changes which require a downward revision in the advance rates are detected by comparing the average net collectible value of the recently collected claims with the difference between the average net collectible value of the performance statistics supporting the current advance rates and one standard deviation from the performance statistics supporting the current advance rates. If the average net collectible value of the recently collected claims is less than or equal to the difference, then a downward revision of the advance rates is triggered. The spreadsheet looks to capture changes which require an upward revision in the advance rates by comparing the average net collectible value of the recently collected claims with the sum of the average net collectible value of the performance statistics supporting the current advance rates and one standard deviation from the performance statistics supporting the current advance rates. If the average net collectible value of the recently collected claims is greater than or equal to the sum, then an upward revision of the advance rates is triggered. If the change in the average net collectible value does not exceed the trigger levels, then the advance rates remain at their present level.

There are a variety of additional statistical techniques beyond using the standard deviation to establish a range around the average net collectible value that can be used in determining the trigger levels for adjusting advance rates. A t-test can be used to construct a confidence interval around the average net collectible value rate. The average net collectible value rate from the recently collected data is then compared with the confidence interval to see if it falls within the confidence interval. An F-test can be used to determine a confidence interval for testing changes in the standard deviation. The standard deviation of the net collectible value rate from the recently collected data is then compared with the confidence interval to see if it falls within the confidence interval. A chi-squared test can be used to determine a confidence interval for testing changes in the standard deviation. The standard deviation of the net collectible value rate from the recently collected data is then compared with the confidence interval to see if it falls within the confidence interval.

If the results of the tests do not indicate a change in the performance statistics, the statistics in the prior performance statistics file are recalculated to update them for the inclusion of the recently collected claims. If the results of the tests indicate a change in the performance statistics for the recently collected records, then, after the advance rates have been changed, the statistics of the recently collected table 45b are stored in the prior performance statistics table 45e. Regardless of the outcome of the tests, both the provider and SPE are transmitted the results using I/O computer 52.

Asset/Liability Management

Figure 47:
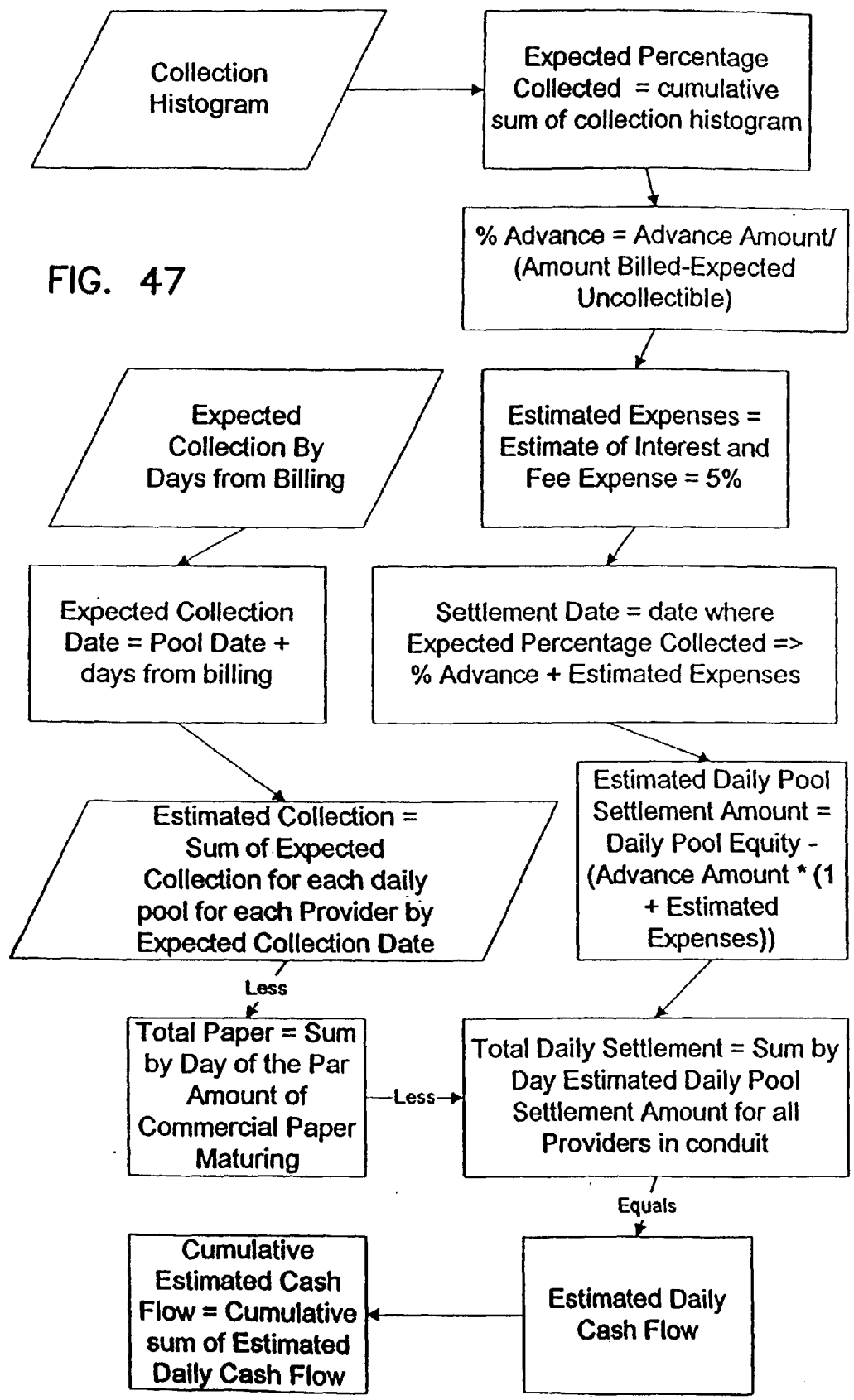
FIG. 47 illustrates an asset/liability management model.

FIG. 47 shows the asset/liability management model executed by software 53 for a commercial paper program. The goal of asset/liability management is to control the providers' exposure to changes in the interest rate on, and liquidity of, commercial paper. This control is achieved by proactively managing the commercial paper being issued by the various conduits. Proactive management allows a provider to specify the funding strategy that they would like to support their receivables. The first step is to estimate the cash collections on each of the daily pools. These estimates are the expected collections calculated as described above and transmitted by the provider sentinel 42 to the central location. Next, the expected collection date is calculated by adding the days from billing to the pool date. The model then sums the expected collection for each daily pool by the expected collection date to generate estimated collection. The second step is to estimate the cash settlement amount for each of the daily pools. This estimate begins by calculating the expected percentage collected histogram. This histogram equals the cumulative sum of the collection histograms. Next, the percentage advance for each daily pool is calculated. Percentage advance equals the advance amount divided by the difference between amount billed and expected uncollectible. Next, an estimate of the interest and fee expenses for the life of the pool is made. The estimated percent expenses is shown here as five percent, but can be changed. Settlement date equals the date on the expected percentage collection histogram where the percentage collected equals or is greater than the sum of the percentage advance plus the estimated expenses. Estimated daily pool settlement amount equals the daily pool equity minus the result of multiplying the advance amount by the estimated percent expenses. Total daily settlements equals the sum by day of the estimated daily pool settlement amounts for all providers in the conduit. An estimate of daily cash flow can now be created. Estimated daily cash flow equals estimated collections minus total paper minus total daily settlements. Cumulative estimated cash flow equals the cumulative sum of estimated daily cash flow. The estimated cumulative cash flow calculated in the asset/liability management is the starting point for helping a provider with its cash flow management. These figures can be used develop investment and bill payment strategies.

Figure 48:
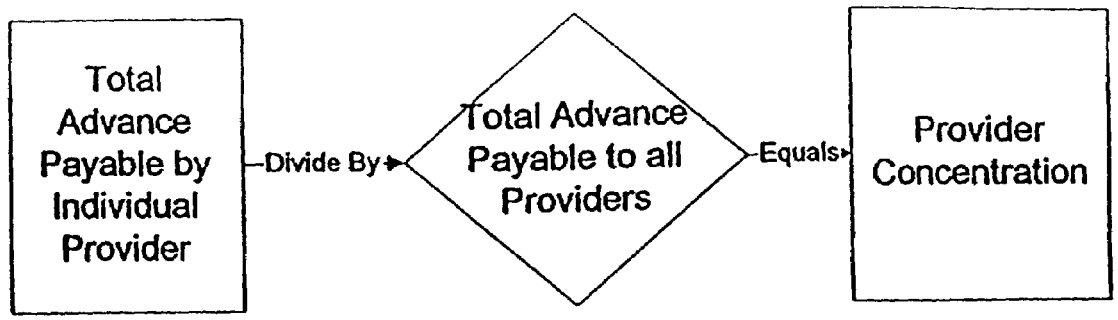
FIG. 48 illustrates the creation of a provider concentration report.

There are several other reports generated by software 53 for the SPE. A provider concentration report looks at the concentration of providers in any given conduit. When rating agencies review their credit rating on a specific SPE, they look for diversification in the SPE's exposure to providers. FIG. 48 depicts how the provider concentration is calculated. For each individual provider in a SPE, the total advance payable to the provider from the balance sheet data 55*k* are divided by the total advance payable made by the SPE. The resulting percentage represents the concentration that an individual provider is to the SPE.

Figure 49:
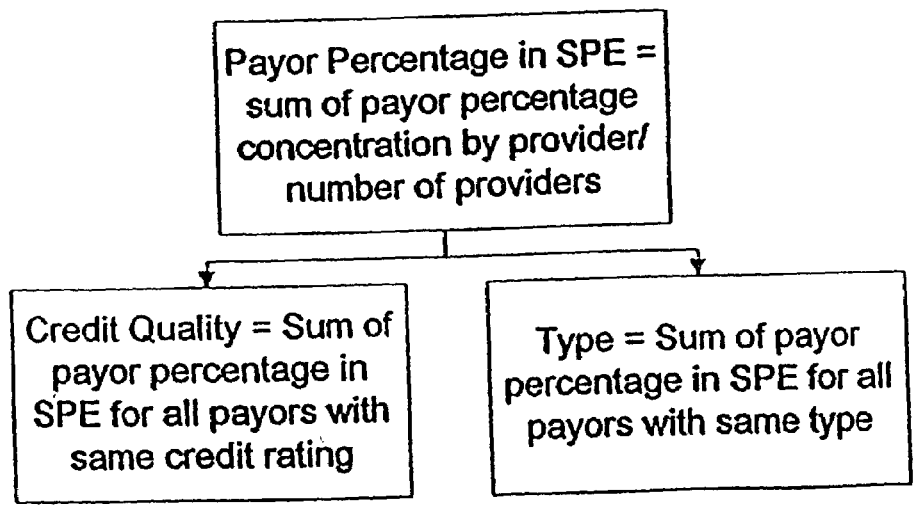
FIG. 49 illustrates the creation of a credit quality and type report.

Rating agencies also look at the SPE's exposure to the payors. A payor exposure report looks at the payors grouped by either credit rating or type of payor. FIG. 49 depicts how these two exposure analysis are calculated by software 53. Both exposures are calculated by first determining the concentration of each individual payor in the SPE. This is found by adding up the percentage concentration of each individual payor at each provider from the payor concentration data sent by the provider sentinel 42 and dividing this sum by the number of providers in the SPE. Exposure by credit quality is then calculated by summing the percentage of each individual payor in the SPE by the credit rating of the payor. Exposure by type of payor is calculated by summing the percentage of each individual payor in the SPE by the type of payor it is. Reports generated by software 53 are stored in an output file for transmission to the provider sentinel system 42 and the SPE sentinel system 62.

The system also generates a credit scoring report. The sentinel system 42 periodically sends the payor effectiveness index to the central location 50. This index measures how much of the amount billed was collected and how quickly the collection occurred. The credit scoring reports shows this index next to the credit quality of the payor's claims paying ability index. The credit quality index ranges from 0.1 to 1 with 0.1 being payors whose claims paying ability is deemed doubtful by the credit rating agencies and 1 being payors whose claims paying ability is deemed extremely strong by the credit rating agencies.

Figure 50:
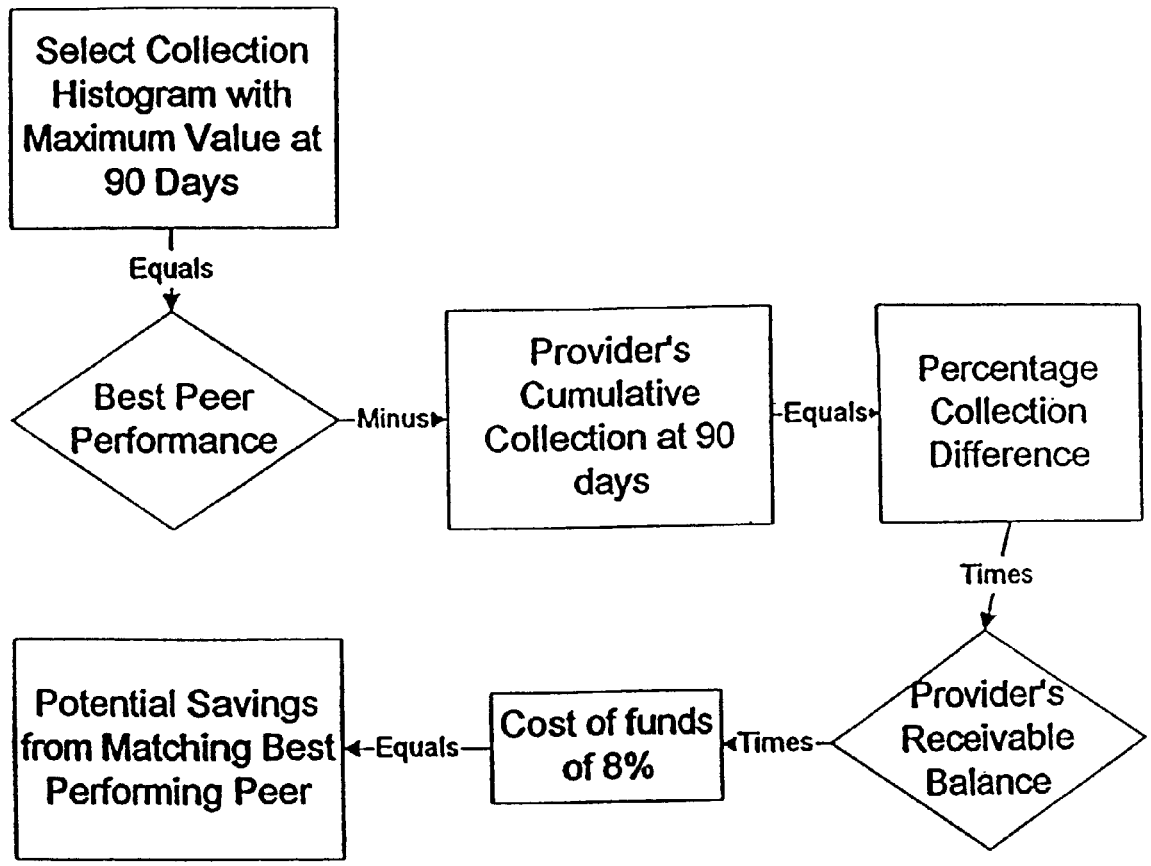
FIG. 50 illustrates the determination of savings from matching a peer's best collection pattern.
Figure 51:
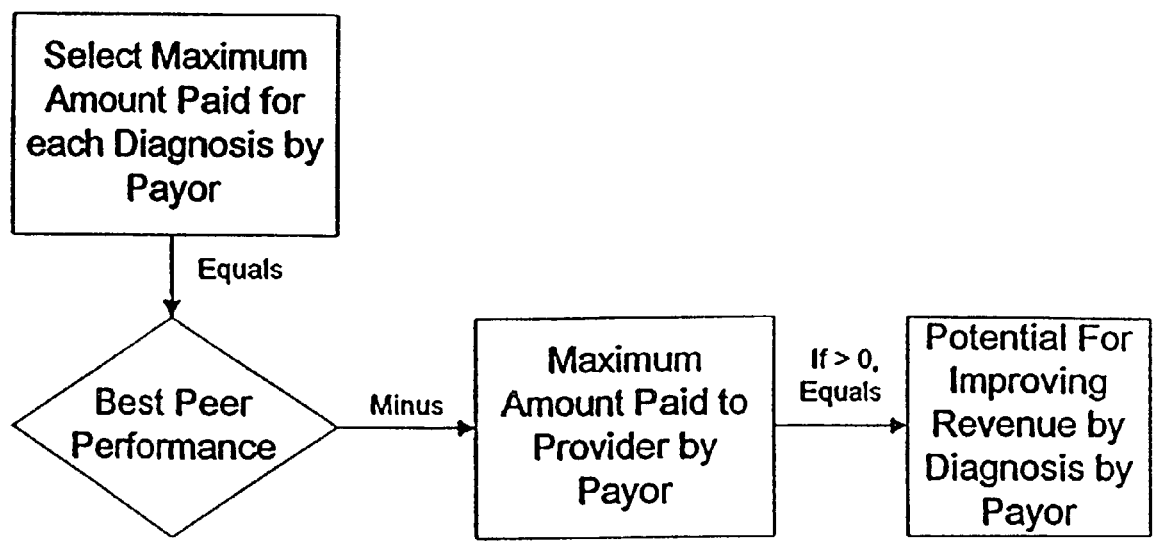
FIG. 51 illustrates the determination of the potential for improving revenue.
Figure 55:
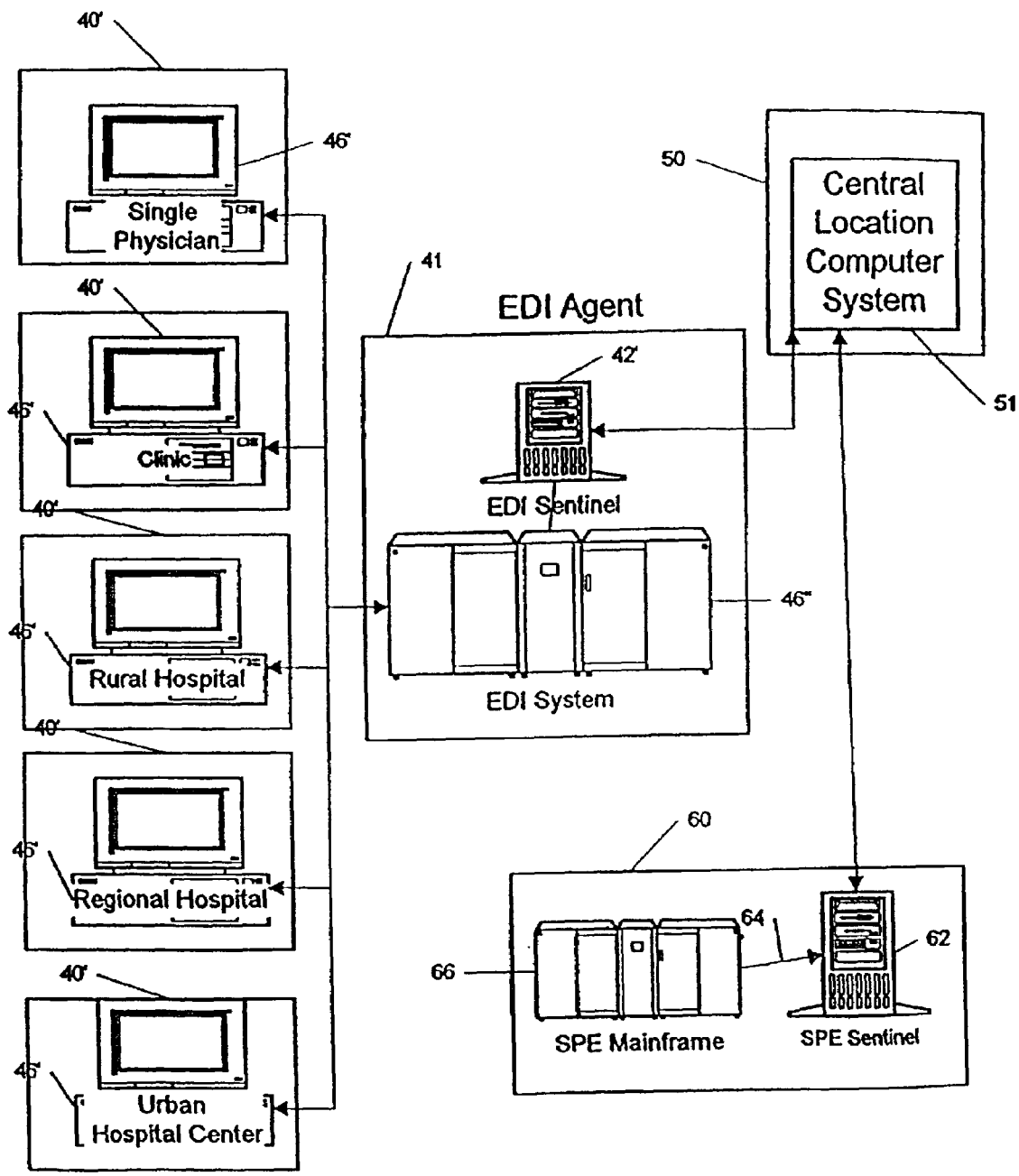
FIG. 55 illustrates an alternate embodiment of the present invention using an EDI system.

Additional reports generated for providers include a peer group comparison report which shows how the provider compared with its peers in the timing of its collections and the net collectability of its claims. These reports are used to illustrate the savings available to the provider from better management of its collections. FIG. 50 shows how software 53 determines the interest savings available to the provider from collecting its receivables as quickly as its best performing peer. The best performing peer is identified as that provider which has the highest percentage of its receivables collected in ninety days. The providers collection histogram is then compared with the provider's collection histogram to show the percentage collection difference by day over the 90 day period. Each day's difference is then multiplied by the provider's average receivables balance. The amount is then summed and multiplied by eight percent a proxy for the average cost of financing this excess receivable balance. The result is the savings available from matching the best performing peer. FIG. 51 shows the earnings available to the provider from collecting the same average amount for each diagnosis by payor as its best performing peer as determined by software 53. The best performing peer is identified for each payor as that peer which has the highest average amount paid for each diagnosis by payor. This provider's average amount paid is then subtracted from each of the best performing peer average amount paid. This difference represents the potential for increased income. The results of these reports are stored in a file for transmission to the provider location or for printing.

Summary

FIGS. 52A, 52B, 53 and 54A–D summarize the origin, transfer and transformation of data moving through system 30. FIGS. 52A and 52B illustrate the input data, functions and output data for the system 30 at the seller's location. FIG. 53 illustrates the input data, functions and output data for the system 30 at the SPE's location. FIGS. 54A, 54B, 54C and 54D illustrate the input data, functions and output data for the system 30 at the central location.

Alternative Uses of Claims Database

As the provider downloads claims information to the sentinel at its location, the claims information is put into a standardized format. One use of the data in this database is for tracking and controlling the provider's participation in a financing program. There are several other equally important uses. This data can be analyzed to create valuable information for a variety of participants in the medical industry. For example, the data can be sorted through to generate statistics on supply usage at a given provider by diagnosis. The results of this analysis allows a provider to measure its profit margin if it is receiving capitated payments from the payors and enters into a capitated supply agreement with its suppliers. For another example, the data could be aggregated across providers to analyze how drug usage patterns influence the cost of treating a specific diagnosis. Pharmaceutical companies are interested in the data from this analysis to show the benefit of their drugs in treating illnesses. Preferably, software 53 includes the capability to perform these functions.

Alternate Embodiments

Electronic Data Interchange Claims

In an alternative embodiment, shown in FIG. 52, the system 30' of the present invention is set up to capture claim records from an electronic claims processor. This claims processor, otherwise known as an electronic data interchange agent, has terminals or computer systems 46' at the offices or locations 40' of physicians, clinics, rural hospitals, regional hospitals or even urban center hospitals. As conventionally operated, the electronic data interchange (EDI) agent's computer system 46" receives claim data from these terminals or computer systems 46' and electronically conveys it to the appropriate payor, such as an insurance company or Medicare or Medicaid. According to the alternate embodiment of the invention, the claims data from the EDI computer system 46" is transferred to a sentinel system 42', where it can be processed on a provider by provider basis and summarized as described above with respect to sentinel system 42 for transmission to the computer system 51 at the central location 50. Reports can be transmitted by the central location computer system 51 directly back to computer systems 46' at the locations 40' using modem transmission.

Use of System 30 for Other Accounts Receivables

As noted above, the system 30 of the present invention is readily adaptable to provide processing for any form of accounts receivable. Instead of processing medical claims, the system can process any form of invoice representing an account receivable, such as attorneys' fees or invoices generated by an industrial supplier. Thus, it shall be understood that the invention is in no way limited to servicing medical providers or medical claims.

Other Periodic Units

The preferred embodiments described above implemented a daily period. It shall be understood, however, that any periodic unit can be used to select claims or invoices to be pooled together and processed pursuant to the principles of the present invention.

Other Pooling Criteria

The preferred embodiments of the present invention pool claims or invoices without regard to the payor of the obligations provided that the payors for the claims or invoices are approved. It is contemplated, however, the selection of accounts receivable for each pool may be done not only on the basis of periodic units, but can also be formed or optimized according to payor. For example, certain pools may have payors which historically pay more quickly than average or a higher percentage of a billed amount that average. This optimization may be accomplished using linear programming, regression analysis or other standard statistical techniques.

Sentinel System Alternative Embodiments

In the preferred embodiments of the invention, the sentinel system 42 is independent of the provider's computer system. It shall be understood, however, that the sentinel software 43 and files and tables 45 can be adapted to execute on the provider's computer system 46, thus eliminating the need for sentinel system 42. However, system 42 is preferred because it avoids the necessity to adapt software 43 and files and tables 45 to each different hardware and software configuration of provider computer systems 46. Similarly, the SPE sentinel software 63 and files can be adapted to execute on the SPE computer system 66.

Central Location Alternative Embodiments

In the preferred embodiment, the central location is remotely located from the SPE and provider or receivable seller. It shall be understood, however, that the central location system 51 can be located at the location of a receivable seller or an SPE. Furthermore, the central location software 53 and files 55 can be adapted to execute and be stored on a provider or SPE computer system.

Conclusion

Thus, there has been described above a computerized system for archiving and storing invoice and claims records and for tracking and controlling a medical provider's participation in an asset back commercial paper program. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled

What is claimed is:

1. Apparatus for processing electronic medical data specifying claims for services rendered, the data specifying an account receivable for a provider of medical services, each claims record including (i) data identifying a patient receiving medical services (ii) a date specifying a date associated with the claim, and (iii) a financial data portion specifying an amount billed for medical services, comprising a first system including one or more processors to execute one or more software components and at least one storage device having stored thereon the one or more software components, wherein the one or more software components are adapted to:

process the electronic medical data and assign claims represented by the data to one or more pools;
    create electronic pool data representative of each pool wherein for each pool the data specifies an aggregate value of the medical services for the claims in the pool against which funds may be advanced;
    electronically transfer data to a second processing system wherein the data transferred specifies at least one claims pool and the aggregate value for the claims pool, and further wherein the transferred data does hot reveal the type of medical service provided to a particular one of the patients receiving medical services for the claims in the at least one pool;

the second system including one or more software components adapted to:

receive and store the data for the at least one claims pool;

process the data for the at least one claims pool in order to facilitate the financing of the claims pool by a financing entity; and one or more processors for executing the one or more software components.

2. Apparatus according to claim 1 further wherein the second system includes at lease one storage device having stored thereon one or more software components adapted to permit a part other than the medical service provider to gain access to the pool data, and further wherein the second system includes one or more processors for executing the one or more software components.

* * * * *